United States Patent [19]
Ota et al.

[11] Patent Number: 5,592,294
[45] Date of Patent: Jan. 7, 1997

[54] COLOR MEASURING APPARATUS WITH POSITION ADJUSTMENT

[75] Inventors: Mitsunobu Ota, Shinshiro; Wataru Yamaguchi; Isamu Nakajima, both of Toyokawa, all of Japan

[73] Assignee: Minolta Co., Ltd., Osaka, Japan

[21] Appl. No.: 410,081

[22] Filed: Mar. 24, 1995

[30] Foreign Application Priority Data

Mar. 30, 1994 [JP] Japan .................................. 6-60949

[51] Int. Cl.$^6$ ......................................................... G01J 3/50
[52] U.S. Cl. ...................... 356/402; 250/226; 250/559.29
[58] Field of Search .................................... 356/402, 405, 356/406, 407, 425, 446, 375; 250/226, 201.1, 201.3, 201.6, 201.7, 201.8, 203.3, 559.2, 559.3, 559.31, 559.37, 559.38, 559.39

[56] References Cited

U.S. PATENT DOCUMENTS

| | | | |
|---|---|---|---|
| 4,317,991 | 3/1982 | Stauffer | 250/201.4 |
| 4,707,138 | 11/1987 | Coatney | 356/402 |
| 4,917,495 | 4/1990 | Steenhoek | 356/328 |
| 5,071,252 | 12/1991 | Matsuura | 356/375 |

*Primary Examiner*—F. L. Evans
*Attorney, Agent, or Firm*—Price, Gess & Ubell

[57] ABSTRACT

An apparatus for measuring a characteristic of an object, the apparatus includes: a light projector which projects light to an object; a photosensor which senses light which has been projected by the light projector and reflected from the object; a calculator which calculates a characteristic of the object based on an output of the photosensor; an angle detector which detects respective angles of the light projector and the photosensor with respect to the object; an adjustment mechanism which adjusts the respective angles of the light projector and the photosensor; and a controller which controls the adjustment mechanism based on a detection result of the angle detector so that the light projector and the photosensor come into their respective desired angles.

7 Claims, 23 Drawing Sheets

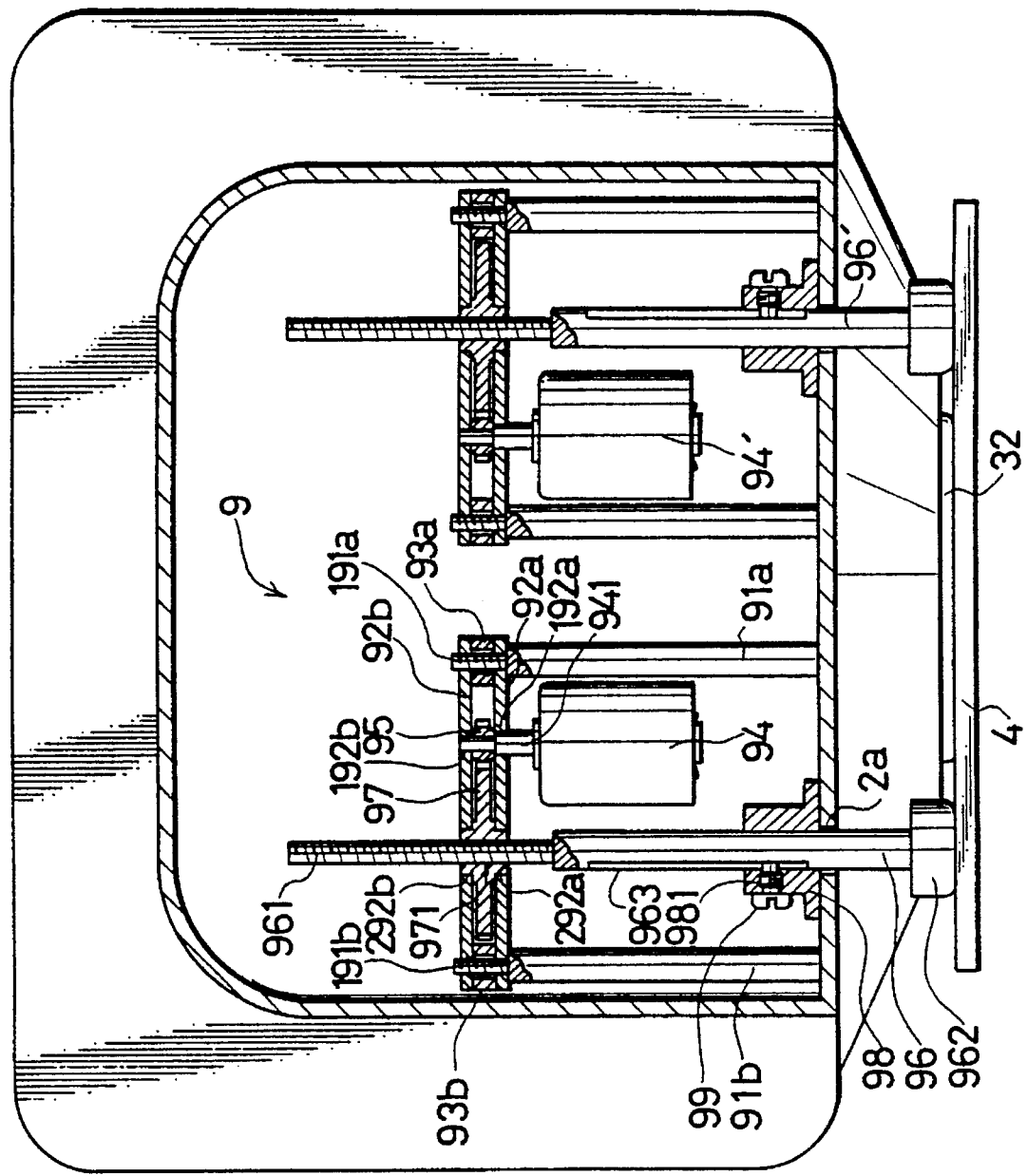

COLOR MEASURING APPARATUS WITH POSITION ADJUSTMENT

BACKGROUND OF THE INVENTION

1. Field of the Invention

This invention relates to a measuring apparatus for measuring a characteristic of an object and, particularly to a measuring apparatus which can be suitably set in a specified posture with respect to the object.

2. Description of Related Art

Some measuring apparatuses require adjustment, during a measuring operation, to attain a specified posture with respect to the object. Examples of these apparatuses are listed below.

In recent years, metallic coating and mica coating have been increasingly used as particularly seen in automotive vehicles. Since these metallic materials display different colors depending upon the angle of observation, it is necessary to accurately determine the color of the surface while observing from various angles. There are known goniocolorimeters and multi-angle colorimeters in which light is projected from one light projector and received at a plurality of angles or light is projected from a plurality of angles and received by one photosensor. With the colorimeters of this type, there exist two kinds of lights: the light diffused and reflected by the surface of the object and the light specularly reflected by metallic particles on the surface layer. Accordingly, a projection angle and a reception angle of the light are a key to colorimetry. Thus, it is particularly necessary to accurately set these angles. It has been a general practice that operators bring the colorimeter into contact with the object on the basis of their own judgments. There have been used non-contact type measuring apparatuses in a production line. The measuring apparatuses of this type are fixed and their posture is adjusted basically by displacing the object.

Japanese Unexamined Patent Publication No. 2-245623 discloses a colorimeter which adapts an apparatus fixing foot member including a magnet for magnetic objects to be measured so as to stabilize the posture of the apparatus with respect to the object using magnetic attraction.

Since the colorimetry requires considerably accurate angle setting as described above, it is difficult to obtain data having good reproducibility according to the conventional posture adjusting method which is performed on the basis of the operator's own judgment. Particularly, it is thought to be almost impossible to accurately adjust the posture of the measuring apparatus with respect to an object having a curved surface. Further, the conventional posture adjustment in the production line requires a belt conveyor for moving the object and the object also needs to be positioned with high accuracy. Thus, a control is not easy. Colorimeters including one light projector and one photodetector for determining the color of the normal object which is not coated with a metallic paint has a similar problem of being unable to obtain reproducible data due to a shift in a direction of specular reflection, if their position relative to the object is not fixedly set.

As for the colorimeter disclosed in the above publication, the posture thereof may be stabilized to a certain degree when the object is of magnetic material and has a flat measurement surface. It is impossible to, depending upon the material of the object and the curved shape of its measurement surface, set the colorimeter in a specified posture so as to obtain data having good reproducibility. Thus, the posture adjustment is obliged to largely depend upon the operators' skills and requires a long time, presenting a problem in terms of efficiency.

Further, the accurate posture adjustment of a measuring apparatus with respect to the object is necessary not only for the aforementioned colorimeters, but also for glossimeters for measuring the gloss of an object and densitometers for measuring the concentration. However, these apparatuses also face the problem of impossibility to set them in a specified posture so as to obtain data having high reproducibility if the posture thereof is adjusted on the basis of the operator's judgment.

SUMMARY OF THE INVENTION

It is an object of the present invention to provide a measuring apparatus which has overcome the problems residing in the prior art.

It is another object of the present invention to provide a measuring apparatus which can detect the posture of an apparatus main body with respect to an object and display a detection result to perform adjustment faster and easier.

It is another object of the present invention to provide a measuring apparatus which can automatically adjust the posture of an apparatus main body based on a result of detection of an apparatus main body posture with respect to an object.

The present invention is directed to a measuring apparatus comprising: a measurement device which measures a characteristic of an object: a posture detector which detects a posture of the measurement device with respect to the object; and a display device which displays the posture of the measurement device detected by the posture detector.

The posture detector may be constructed by a light projector which projects a spotlight to a specified portion of the object; a photosensor which senses light which has been projected by the light projector and reflected from the specified portion of the object; and a judging device which judges the posture of the measurement device based on an output of the photosensor.

It may be appreciated to further provide a distance detector which detects a distance from the measurement device to the object. The display device displays the distance to the object detected by the distance detector.

Also, it may be appreciated to further provide a temperature detector which detects a temperature of the object. The display device displays the temperature of the object detected by the temperature detector. There may be further provided a correction device which corrects a measurement result of the measurement device based on the detected temperature.

Moreover, it may be appreciated to further provide an adjustment mechanism which adjusts the posture of the measurement device with respect to the object. There may be further provided a controller which controls the adjustment mechanism based on a detection result of the posture detector to adjust the posture of the measurement device into a desired one.

The measurement device may be adapted for measuring an optical characteristic of the object. The measurement device may be constructed by a light projector which projects light to the object: photosensor which senses light which has been projected by the light projector and reflected from the object; and a calculator which calculates an optical characteristic of the object based on an output of the photosensor. Further, the measurement device may be adapted for measuring color of the object, and the calculator calculates a color value of the object.

The present invention is directed to a measuring apparatus comprising: a measurement device which measures a characteristic of an object; a posture detector which detects a posture of the measurement device with respect to the object; and an adjustment device which adjusts the posture of the measurement device into a desired one based on a detection result of the posture detector.

It may be appreciated to further provide a distance detector which detects a distance from the measurement device to the object. The adjustment device may adjust the distance of the measurement device to the object into a desired one.

It may be appreciated to further provide a temperature detector which detects a temperature of the object: and a correction device which corrects a measurement result of the measurement device based on the detected temperature.

The adjustment device may be constructed by an adjustment mechanism which adjusts the posture of the measurement device with respect to the object; and a controller which controls the adjustment mechanism so that the measurement device comes into a desired posture.

It may be preferable to further provide a display device which displays the posture of the measurement device detected by the posture detector.

The present invention is directed to an apparatus for measuring color of an object, the apparatus comprising: a primary light projector which projects light to an object; a primary photosensor which senses light which has been projected by the light projector and reflected from the object; a calculator which calculates a color value of the object based on an output of the primary photosensor; an angle detector which detects respective angles of the primary light projector and the primary photosensor with respect to the object; an adjustment mechanism which adjusts the respective angles of the primary light projector and the primary photosensor: and a controller which controls the adjustment mechanism based on a detection result of the angle detector so that the primary light projector and the primary photosensor come into their respective desired angles.

The angle detector may be constructed by a secondary light projector which project a spotlight to the object: a secondary photosensor which senses light which has been projected by the secondary light projector and reflected from the object: a judgment device which judges based on an output of the secondary photosensor the respective angles of the primary light projector and the primary photosensor with respect to the object.

It may be appreciated to further provide a display device which displays the detected angles of the primary light projector and the photosensor.

There may be further provide a housing which accommodates the primary light projector, the primary photosensor, the calculator, the angle detector, and the adjustment mechanism. The adjustment mechanism may be constructed by a base member which carries the primary light projector and the primary photosensor, and is movable relative to the housing; and a driver which drives the base member to adjust the respective angles of the primary light projector and photosensor. Also, the adjustment mechanism may be constructed by a support member which supports a specified portion of housing, and is movable relative to the housing; and a driver which drives the support member to adjust the respective angles of the primary light projector and photosensor.

It may be appreciated that light is projected to the object at a single angle by the primary light projector while reflected light is sensed at a plurality of different angles by the photosensor. Conversely, it may be appreciated that light is projected to the object at a plurality of different angles by the primary light projector while reflected light is sensed at a single angle by the photosensor.

With the above-constructed measuring apparatus, there is provided a posture detector which detects a posture of the measurement device with respect to an object before measuring a characteristic of the object. A detection result is displayed by the display device. Accordingly, an operator is allowed to adjust the posture of the measurement device with respect to the object while viewing the displayed detection result. This leads to a more rapid, easy and accurate adjustment. Thus, an accurate measurement result with high reproducibility can be obtained.

Also, there is provided an adjustment device which adjusts the posture of the measurement device with respect to the object based on a detection result of the posture detector. This will make it possible to carry out the posture adjustment of the measurement device automatically. Accordingly, the posture adjustment can be made rapidly and accurately. Thus, an accurate measurement result with high reproducibility can be obtained.

These and other objects, features and advantages of the present invention will become more apparent upon a reading of the following detailed description and accompanying drawings.

BRIEF DESCRIPTION OF THE DRAWINGS

FIG. 4 is a rear view in section showing a posture adjusting mechanism of the first colorimeter;

DETAILED DESCRIPTION OF THE PREFERRED EMBODIMENTS OF THE INVENTION

Figure 1:
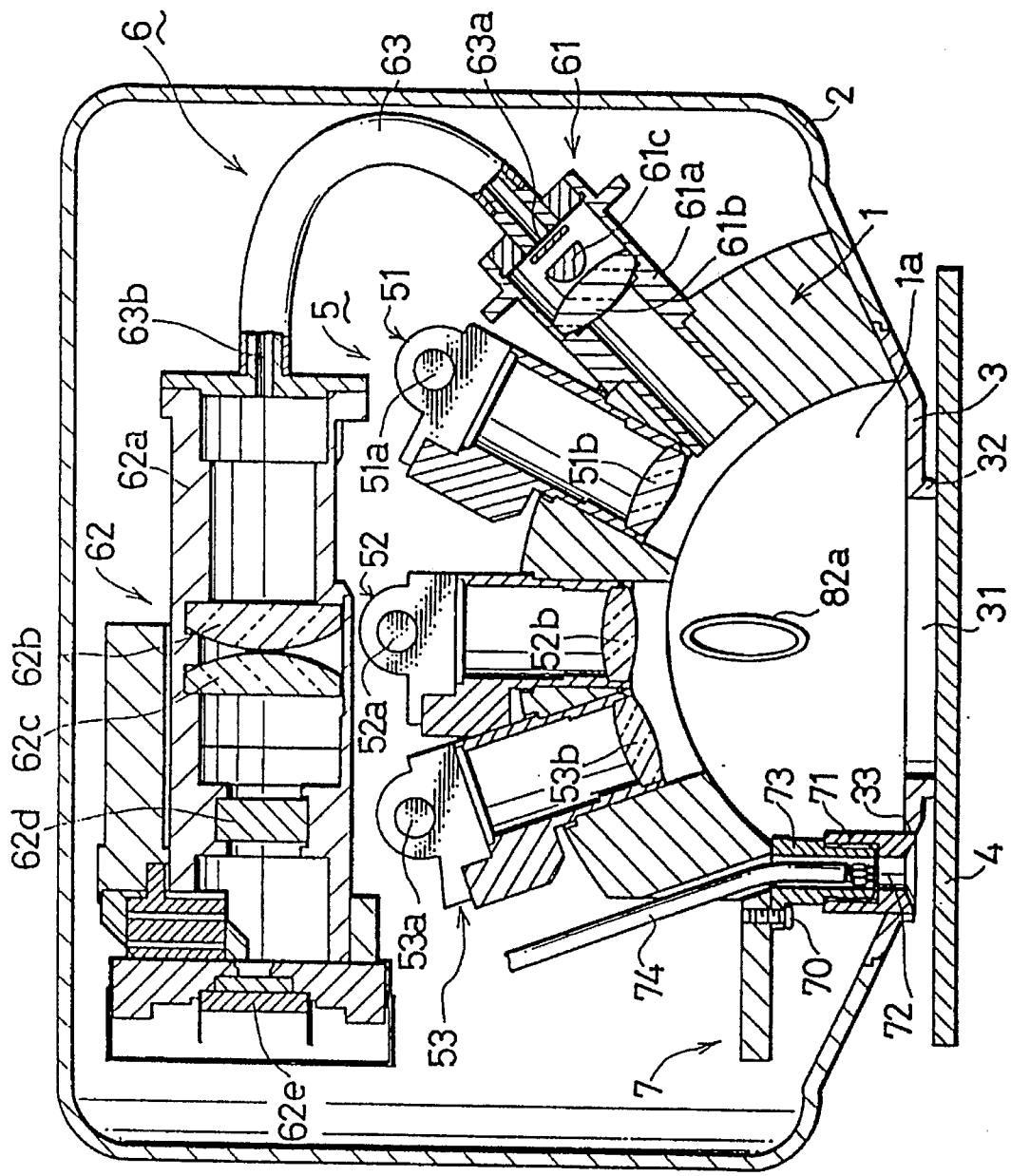
FIG. 1 is a front view in section showing a mechanical construction of a colorimeter as a first embodiment of the present invention.
Figure 2:
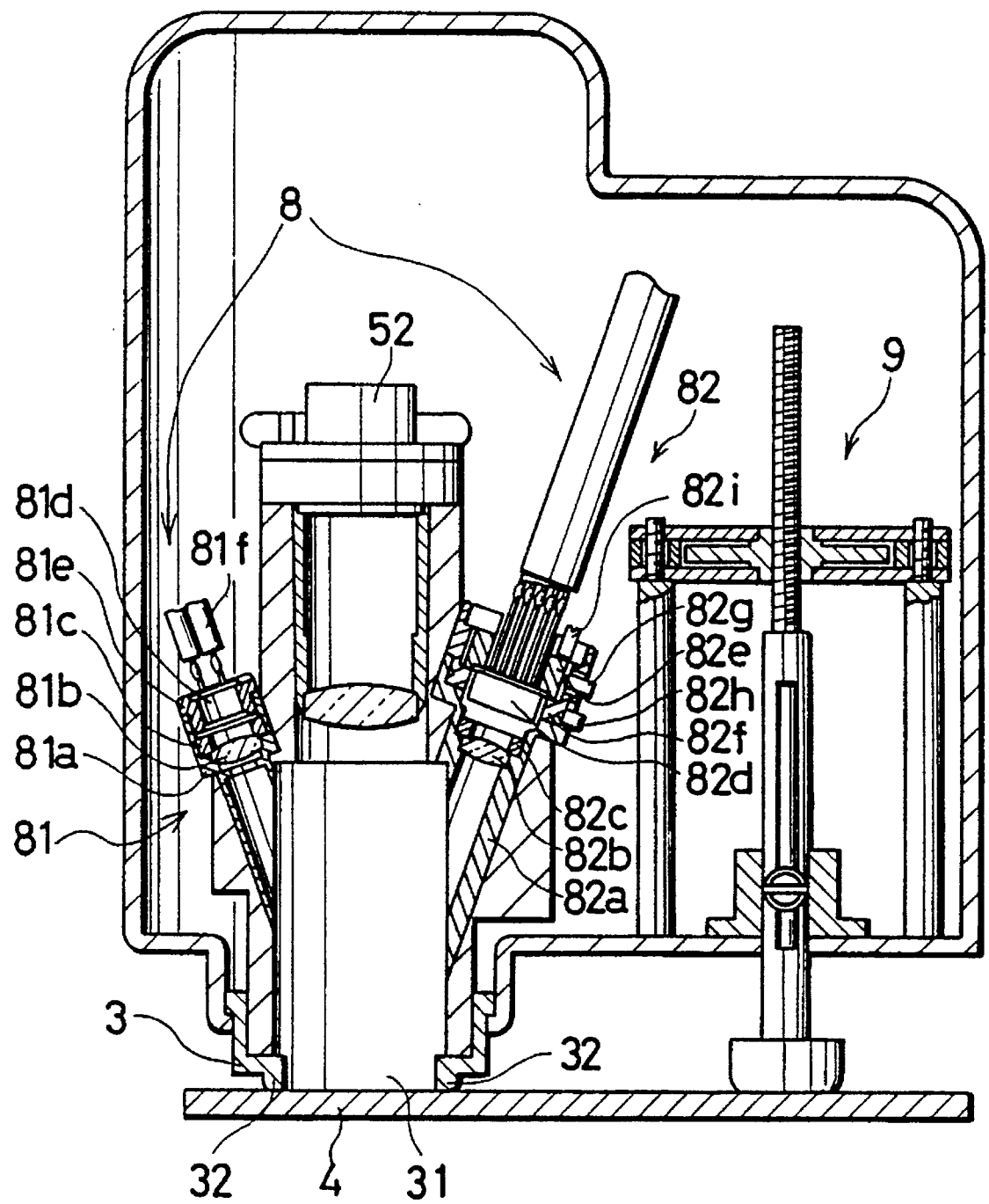
FIG. 2 is a side view in section showing the mechanical construction of the first colorimeter.

FIGS. 1 to 4 show a multi-angle spectral colorimeter as a first embodiment of the present invention. FIGS. 1 and 2 are a sectional front view and a sectional side view of this colorimeter, respectively, FIG. 3 is a diagram showing a construction of a sensor provided in a posture detector, and FIG. 4 is a sectional rear view showing a posture adjusting mechanism provided in this colorimeter.

In FIG. 1, indicated at 1 is an optical base member of the colorimeter, at 2 a housing for accommodating the optical base member 1, and at 3 a measurement foot member secured on the optical base member 1. The foot member 3 and the housing 2 are closely in contact with each other so as to securely block entrance of external light. Below the optical base member 1, there is formed a measurement space 1a of substantially semicircular shape when viewed from the front.

Inside the housing 2, there are arranged a light projector unit 5 for projecting light to an object 4 to be measured, a photosensor unit 6 for receiving the light reflected by the surface of the object, a temperature detector 7, a posture detector 8 and posture adjusting mechanisms 9.

The foot member 3 is disposed in such a position as to cover the measurement space 1a and is formed at its bottom with an opening 31 having a specified shape such as a circle or rectangle and facing the object 4. Around or near the periphery of the opening 31, there is formed a projection 32 which projects downward by a specified distance. The surface of the object 4 is brought into contact with the projection 32.

The light projector unit 5 and the photosensor unit 6 constituting a colorimetric optical system are secured on the optical base member 1. They are disposed on a plane perpendicularly intersecting a surface of the object 4. This plane is hereinafter called the X-plane.

The light projector unit 5 includes three light projectors 51, 52 and 53 directed toward and arranged radially with respect to the center of the opening 31. The light projector 51, 52 and 53 form angles +27.5°, 0° and −20° with respect to another plane which perpendicularly intersects both the surface of the object 4 and the X-plane, and passes the center of the opening 31. This another plane is hereinafter called the Y-plane.

Indicated at 51a, 52a and 53a are light sources such as halogen lamps and xenon lamps for emitting light of specified color temperature. Beams of light emitted from the light sources 51a, 52a and 53a are focused into parallel beams by lenses 51b, 52b and 53b disposed ahead, respectively, and projected onto the center of the opening 31, i.e., the surface or surface layer of the object 4.

The photosensor unit 6 includes a light receiving unit 61 and a sensing unit 62 which are connected by an optical fiber 63. The light receiving unit 61 is directed toward the center of the opening 31 and forms an angle of, e.g., 45° with respect to the Y-plane. Thus, beams of light are incident upon the light receiving unit 61 as reflected lights from the surface or surface layer of the object 4 from directions of angles 27.5°, 45° and 65°.

The light receiving unit 61 includes a barrel 61a for guiding the incident beams (for assuring directivity), a convex lens 61b and a hemispherical lens 61c disposed behind the lens 61b. The lenses 61b and 61c are secured on the barrel 61a. A leading end 63a of the optical fiber 63 is located immediately behind the hemispherical lens 61c. Thus, the reflected beams are efficiently focused and introduced to the fiber 63 by the lenses 61b and 61c.

The sensing unit 62 includes a barrel 62a, cylindrical lenses 62b to 62d, and a photosensor 62e of spectral type. A rear end 63b of the optical fiber 63 is located at a leading end of the barrel 62a. The lenses 62b to 62d are arranged such that their optical axes correspond with one another. The photosensor 62e is arranged behind the lenses 62b to 62d on the same optical axis therewith. The beam introduced by way of the fiber 63 is converted into a beam having a rectangular cross-section by the cylindrical lenses 62b to 62d and introduced to a sensing surface of the photosensor 62e. The received beam is converted into the beam having a rectangular cross-section because the spectral type photosensor 62e is of a rectangular shape in which a plurality of photocells are arrayed in spectral directions. The use of the optical fiber 63 allows the sensing unit 62 to be disposed in a specified space within the housing 2 or in a position away from the X-plane, thereby enabling fabrication of a smaller size apparatus and facilitating a layout thereof.

The temperature detector 7 is mounted on the optical base member 1 by means of a screw 70 and a leading end thereof is fitted in a hole 33 of a specified diameter which is formed in a specified position of the downward facing surface of the foot member 3, so that it faces the surface of the object 4. The temperature detector 7 includes a hollow cylindrical holder 71 fitted in the hole 33, a thermopile 72 as a thermally sensitive element which is secured on the holder 71, a retainer 73 fitted in or screwed to the holder 71 for retaining the thermopile 72, and two lead wires 74 for sending electrical detection signals. A sensing surface of the thermopile 72 is away from the surface of the object 4 substantially by a vertical distance of the projection 32. This thermopile 72 includes a pair of thermocouples of one type, which generates and outputs a voltage difference corresponding to the surface temperature of the object 4 between the two lead wires 74. In this way, the surface temperature of the object 4 is made measurable.

As shown in FIG. 2, the posture detector 8 is secured on the optical base member 1, and positioned along the Y-plane. The posture detector 8 does not hinder the color measurement. The posture detector 8 includes a light projector unit 81 and a photosensor unit 82. The units 81 and 82 are both directed toward the center of the opening 31 and are symmetrically arranged with respect to the X-plane to form, for example, +20° and −20° with respect to the X-plane.

It should be appreciated that the posture detector 8 is not necessarily positioned on the Y-plane if it does not stand as a hindrance to the colorimetric optical system. For example, it may be positioned on the X-plane or on a plane which is perpendicular to the surface of the object 4 but inclined with respect to the X-plane.

It is preferred that the units 81 and 82 form the same angle with respect to the X-plane, but the angles may be slightly different so long as the light reception level at the photosensor unit 82 is sufficient for measurement. Further, the angle is not particularly limited to 20°, but may be changed suitably according to the disposed position of the posture detector 8.

The light projector unit 81 includes a barrel 81a, a projection lens 81b, a lens holder 81c, a light emitting diode (LED) 81d, and a hollow cylindrical holder 81e. The lens 81b and the lens holder 81c are secured on the barrel 81a. The LED 81d which acts as a light source is disposed behind the lens holder 81c, and is adhered to the holder 81a. The holder 81e is fitted into the barrel 81a from the rear end of the barrel 81a and coupled therewith by an unillustrated screw. The leading end of the barrel 81a is formed into a hollow cylindrical portion projecting from a position immediately before the lens 81b. This cylindrical portion projects into the measurement space 1a in order to to emit light emitted from the LED 81d to the center of the opening 31. A lead wire 81f for causing the LED 81d to emit light is connected with the rear end of the light projector unit 81. It should be appreciated that, in place of the LED, tungsten lamp or laser may be used as a light source.

The photosensor unit 82 includes a barrel 82a. A lens 82b and a lens holder 82c are secured on the barrel 82a. A silicone photodiode (SPD) 82d as a photosensor is disposed behind the lens holder 82c integrally with a substrate 82a. The SPD 82d is adhered to the substrate 82e. The substrate 82e is fitted into a cylindrical holder 82f which is fitted into the barrel 82a, and is secured thereon by means of a fixing screw 82i. An adjustment screw 82g is adapted to adjust the position of the SPD 82d. The position of the SPD 82d is adjusted by rotating the adjustment screw 82g after loosening the fixing screw 82i and fixed in a specified position by tightening the holder 82f.

The holder 82f is fitted on the rear end of the barrel 82a and secured by a fixing screw 82h. The leading end of the barrel 82a is formed into a hollow cylindrical portion projecting from a position immediately before the lens 82b. This cylindrical portion projects into the measurement space 1a in order to introduce the light reflected by the surface of the object 4 to the lens 82b. The lens 82b focuses the reflected light into a spot light LS1 (see FIG. 3A) having a specified diameter which is introduced onto a sensing surface of the SPD 82d. Lead wires for sending a electrical signal representing a quantity of received light to a processor to be described later are connected with the rear end of the SPD 82d. It should be appreciated that a charge coupled device (CCD) may be used as a photosensor in place of the SPD.

Figure 3A:
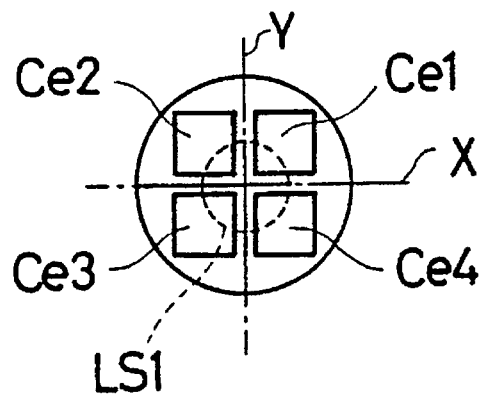
FIGS. 3A, 3B and 3C are diagrams showing a sensor provided in a posture detector, FIG. 3A showing a construction of the sensor, FIG. 3B showing directions of movements of a spot light on a cell due to an inclination of an apparatus main body relative to the sensor, FIG. 3C showing directions of movements of the spot light on the cell due to an inclination of the apparatus main body relative to the sensor when the sensor is not accurately positioned with respect to a circumferential direction.
Figure 3B:
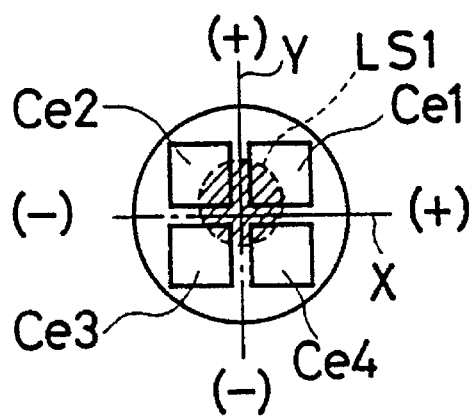
Figure 3C:
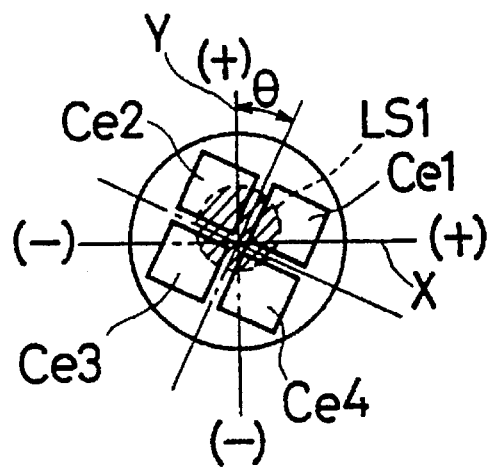

FIGS. 3A, 3B and 3C are plan views of the SPD 82d when viewed from the sensing surface thereof. Four equally sized cells are arranged at four circumferential positions. In the description below, these four cells are referred to as Ce1 to Ce4 in relation to the spot light LS1 for the sake of convenience.

There is described the mounting position of the SPD 82d and the angular adjustment thereof in the circumferential direction.

If the colorimeter main body inclines in a plus direction (clockwise direction about the center of the opening 31 in FIG. 1) on the X-plane, the quantities of light received by the cells Ce2 and Ce3 increase. If the colorimeter main body inclines in a minus direction on the X-plane, the quantities of light received by the cells Ce1 and Ce4 increase. Further, if the colorimeter main body inclines in a plus direction (clockwise direction about the center of the opening 31 in FIG. 2) on the Y-plane, the quantities of light received by the cells Ce1 and Ce2 increase. If the colorimeter main body inclines in a minus direction on the Y-plane, the quantities of light received by the cells Ce3 and Ce4 increase. Accordingly, when the main body is in a vertical posture with respect to the surface of the object (reference posture), an adjustment is made, for example, at a stage of production so that the quantities of light received by the four cells Ce1 to Ce4 correspond with one another.

It is difficult to finely adjust the position of the SPD 82d so that the light from the LED 81d is uniformly projected onto the four cells Ce1 to Ce4 when the colorimeter main body is in the reference posture. Further, it takes a long time to make such adjustment. Accordingly, the uniform projection of light may be realized by signal processing as follows.

This adjustment can be made during a step of correcting characteristic variations of the respective apparatuses using a reference white correction plate. More specifically, the light reflected by the white correction plate is received by the cells Ce1 to Ce4 and output voltages from the cells Ce1 to Ce4 according to the quantities of the received light are read. Correction factors of the sensing surfaces of the respective cells Ce1 to Ce4 for the output voltages are calculated and read.

If it is assumed that the output voltages from the cells Ce1, Ce2, Ce3 and Ce4 are V1, V2, V3 and V4, respectively, a correction factor K1 of the cell Ce1 is (Vt/4)/V1, a correction factor K2 of the cell Ce2 (Vt/4)/V2, a correction factor K3 of the cell Ce3 (Vt/4)/V3, and a correction factor K4 of the cell Ce4 (Vt/4)/V4. It should be noted that Vt=V1+V2+V3+V4. By multiplying the output voltages of the cells by the corresponding correction factors K1 to K4 during an actual measurement, the output voltage from the respective cells can correspond with one another when the colorimeter main body is in a vertical posture with respect to the surface of the object 4.

The angle of the SPD 82d is also adjusted in this step of adjustment. The cells Ce1 to Ce4 constituting the SPD 82d need to accurately correspond to the four quadrants defined by the mutually orthogonal X-plane and Y-plane (state shown in FIG. 3A). Unless the respective cells correspond to the X- and Y-planes of the apparatus main body (state shown in FIG. 3C), the actual inclination of the apparatus main body does not coincide with the calculated inclination. As a result, the angle of projection and the angle of reception with respect to the surface of the object differ in the colorimetric optical system, making it impossible to obtain accurate measurement results.

The angle of the SPD 82d is adjusted by inclining the apparatus main body in -the plus (or minus) direction on the X-plane (or Y-plane) and checking variations of the output voltages from the respective cells.

If the respective cells are mounted so as to accurately correspond with the respective quadrants as shown in FIG. 3B, the spot light LS1 moves toward the sensing surfaces of the cells Ce1 and Ce2 if the apparatus main body is inclined in the plus direction on the Y-plane as described above. Accordingly, the output voltages V1 and V2 from the cells Ce1 and Ce2 increase, whereas the output voltages V3 and V4 from the cells Ce3 and Ce4 decrease. If, at this time, the relationship of the output voltages of the cells is constantly such that (V1+V4)=(V2+V3), it means that the cells are accurately set. In order to set them more accurately, a confirmation of whether or not (V1+V2)=(V3+V4) may be made on the X-plane besides or instead of on the Y-plane.

On the other hand, if the cells are mounted while being displaced with respect to the respective quadrants as shown in FIG. 3C, the spot light LS1 moves toward the sensing surfaces of the cells Ce1 and Ce2 if the colorimeter main body is inclined in the plus direction on the Y-direction. Accordingly, the output voltages V1 and V2 from the cells Ce1 and Ce2 increase, whereas the output voltages V3 and V4 from the cells Ce3 and Ce4 decrease. The results seem to be the same as the one shown in FIG. 3B. However, at this time, the output voltages of the respective cells are not in an equal relationship since (V1+V4)<(V2+V3) because V1 <V2 as is clear from FIG. 3C. In this case, although the colorimeter main body is actually inclined in the plus direction on the Y-plane, the inclination thereof is calculated to be in a composite direction of the plus direction on the Y-plane and the plus direction on the X-plane. Accordingly, the angle adjustment is made by rotating the holder 82f after loosening the fixing screw 82h so that (V1 +V4)=(V2+V3), and then the fixing screw 82h is tightened again. It should be appreciated that the number of cells may be three and they may be arranged at an angle of 120°. In this case, a displacement of inclination may be calculated for each vector component.

The posture adjusting mechanisms 9 are mounted at a rear part within the housing 2 as shown in FIG. 2. This mechanism 9 is shown in detail in FIG. 4. The mechanisms 9 are mounted on a plane in parallel with the X-plane equidistantly from the center of the opening 31 (they are mirror images each other with respect to the center of the opening 31). Since the posture adjusting mechanisms 9 have each an identical construction, description is given only to one of them.

Shafts 91a and 91b have a specified length and project upward from the bottom surface of the housing 2 when spaced apart by a specified distance. Small diameter portions 191a and 191b are formed at the top of the shafts 91a and 91b, respectively. Two gear plates 92a and 92b are mounted between the small diameter portions 191a and 191b with cylindrical spacers 93a and 93b of a specified size therebetween. Motor shaft holes 192a, 192b and gear holes 292a, 292b are formed at their respective corresponding positions of the gear plates 92a and 92b near the shaft 91a and near the shaft 91b. A shaft 941 of a motor 94 mounted below the gear plates 92a and 92b is fitted and rotatably supported in the motor shaft holes 192a and 192b. The motor 94 is secured at a specified position of the optical base member 1. A gear 95 is rotatably secured on the motor shaft 941 between the gear plates 92a and 92b.

The housing 2 is formed with a through hole 2a right below the gear holes 292a and 292b. A prism-like support leg 96 is slidably fitted in the through hole 2a. An upper half of the support leg 96 is formed into a threaded portion 961. A gear 97 is rotatably mounted between the gear plates 92a and 92b using the gear holes 292a and 292b as bearings. The diameter of the gear 97 is set such that it is meshable with the gear 95. The gear 97 is formed in its center with an internally threaded hole 971 of a specified diameter. The threaded portion 961 is engageably fitted in the internally threaded hole 971.

A foot 962 covered with soft material is formed at the bottom of the support leg 96 so that it will not damage the surface of the object when it is brought into contact with the object 4. Since the foot 962 is adapted to stably keep the colorimeter main body in the adjusted posture, its material should be elastically deformable to a small degree despite its softness, or should be of a thin layer.

The support leg 96 is held upright by a gear 98 at the position of the through hole 2a, thereby preventing it from shaking. The support leg 96 is formed on one surface with a groove 963 of a specified length which extends along the longitudinal direction of the leg 96. Indicated at 99 is a rotation restricting key of e.g., pin-like shape which comes into contact with the groove 963 of the support leg 96 through a hole 981 formed in the bearing 98. When the key 99 is in contact with the groove 963, the support leg 96 is allowed to vertically slide within a range corresponding to the length of the groove 963 although its rotation is restricted.

When the motor 94 rotates in a specified direction, its rotational force is transmitted to the gear 97 through the gear 95. The rotational force applied to the gear 97 is transmitted to the threaded portion 961 in engagement with the internally threaded hole 971. Since the rotation of the threaded portion 961 is restricted by the key 99 at this stage, the rotational force is translated into a linear movement. In other words, as the motor 94 rotates, the projecting distance of the support leg 96 projecting from the bottom of the apparatus main body is made variable.

A DC motor, a stepping motor, a supersonic motor or like motor can be used as the motor 94. The use of a linear motor obviates the need for the gears 97 and 95, thereby simplifying the construction.

The posture adjustment is performed in accordance with the detection data from the posture detector 8 to be described below. For example, if the posture is inclined in the plus direction on the X-plane, the projecting distance of the left side support leg 96 in FIG. 4 is made longer (forward rotation of the motor 94) and that of the other support leg 96' is made shorter (reverse rotation of the motor 94'). Similarly, if the posture is inclined in the minus direction on the X-plane, the projecting distances of the support legs 96 and 96' are made shorter and longer, respectively. If the posture is inclined in the plus direction on the Y-plane, the projecting distances of the support legs 96 and 96' are both made longer. If the posture is inclined in the minus direction on the Y-plane, the projecting distances of the support legs 96 and 96' are both made shorter. If the posture is inclined with respect to both the X-plane and the Y-plane, it can be gradually adjusted to the vertical posture by repeating the above operation. In this case, the control may be such that the projecting distances of the support legs 96 and 96' with respect to both the X-plane and the Y-plane are calculated and the motors 94 and 94' are driven in accordance with the calculation result.

The projecting distance of the support leg 96 is controlled by detecting a rotation pulse from a rotary encoder concentrically mounted on the rotatable shaft 941 of the motor 94 or the gears 95 and 97. Alternatively, the projecting distance of the support leg 96 to realize the reference position may be controlled in accordance with a drive signal sent to the motor 94 or a driving time of the motor 94 when the motor 94 is driven at a constant speed.

The controller to perform the posture adjustment gives a warning stops the driving of the motor 94 when the engaged position of the threaded portion 961 with the internally threaded hole 971 approaches a specified position, e.g., a position 2 millimeter away from the upper or lower limits of the movable range of the threaded portion 961. This prevents an undesirable event where the internally threaded hole 971 is caught at the end of the threaded portion 961 and cannot be moved in the opposite direction.

Figure 5:
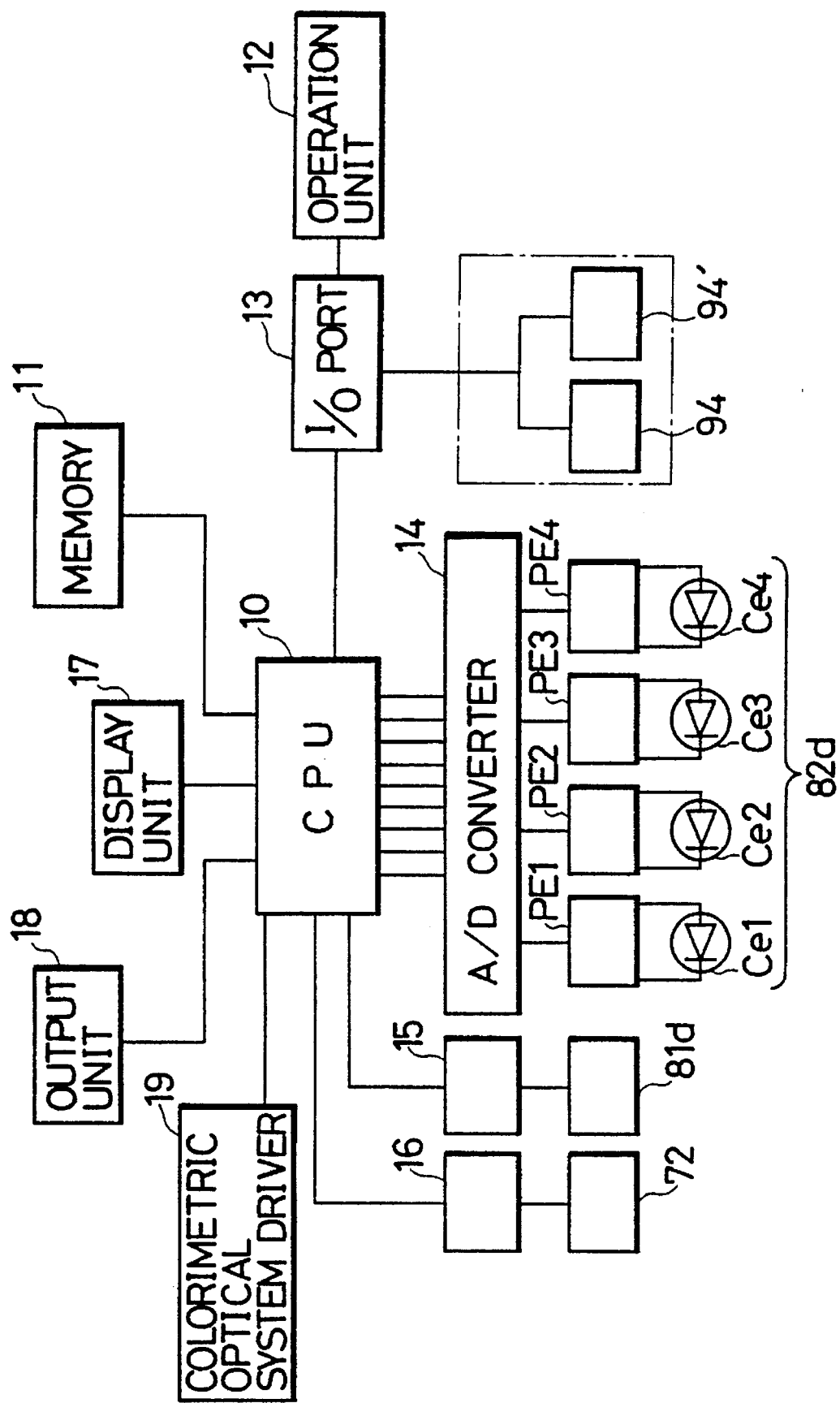
FIG. 5 is a circuit block diagram showing an electrical construction of the first colorimeter.

FIG. 5 is a circuit block diagram showing an electrical construction of the first colorimeter.

Indicated at 10 is a microcomputer for centrally controlling an overall operation of the colorimeter. This component is hereinafter referred to as CPU. Programs for the color measurement are stored in the CPU 10. A correction data for the colorimetry and a correction data necessary to detect the position are stored in the memory 11. In the memory 11, there are also stored characteristic data of the object such as "sample number, colorant, color" in correspondence with thermochromism for each sample number. When an object having characteristic data which are not stored in the memory 11 is measured, these data may manually be input by an operator.

Thermochromism refers to a temperature characteristic peculiar to a colorant (see TABLE-1). The color of the colorant is known to change with temperature. Generally, a distribution of spectral reflectance of the colorant shifts toward a longer wavelength range as temperature increases, while shifting toward a shorter wavelength range as temperature decreases. Even for the same colorant, the higher the chroma is, the greater the color value changes. If the colorants differ, a color variation differs even for the same color. TABLE-1 shows a temperature characteristic per 10° C. for the colorants of intermediate chroma, i.e., a variation Δ. It should be appreciated that TABLE-1 is expressed L*a*-b* color coordinate systems. E*ab denotes a color difference.

TABLE 1

| COLOR | ΔL* | Δa* | Δb* | Δ*ab |
|---|---|---|---|---|
| White | 0.00 | 0.00 | 0.00 | 0.00 |
| Red | −0.51 | −0.94 | −0.86 | 1.37 |
| Orange | −0.15 | −0.01 | −0.35 | 0.39 |
| Yellow | −0.29 | +0.65 | −0.02 | 0.71 |
| Yellow Green | −0.06 | +0.53 | +0.21 | 0.58 |
| Green | −0.25 | +0.54 | −0.03 | 0.60 |
| Cyan | −0.09 | +0.25 | +0.01 | 0.26 |
| Purple | +0.03 | −0.01 | +0.05 | 0.06 |
| Deep Pink | +0.02 | +0.02 | −0.06 | 0.07 |
| Brown | −0.08 | −0.07 | −0.03 | 0.11 |

Indicated at 12 is an operation unit including a keyboard. If necessary, an instruction and specified data such as characteristic data of the object are input by means of the operation unit 12. An I/O port 13 is adapted to send the data input by means of the operation unit 12 to the CPU 19 or to send the control data from the CPU 10 to the motors 94 and 94' to be described later.

Indicated at PE1 to PE4 are photoelectric conversion circuits for converting the signals representing the quantities of light received by the cells Ce1 to Ce4 constituting the SPD 82d into voltage level signals representing output voltages having specified linear relationships with the quantities of the received light. The output voltages from the photoelectric conversion circuits PE1 to PE4 are converted into digital data by an analog-to-digital (A/D) converter 14 and read to the CPU 10. Indicated at 15 is a light projector driver for causing the LED 81d to emit light for the posture detection in accordance with a control signal from the CPU 10. Indicated at 16 is a data processor for reading the output voltage from the thermopile 72 and converting this voltage into a temperature data which defines a specified linearity between this voltage and a measured temperature. Indicated at 17 is a display unit which is disposed at an easily visible external position of the colorimeter main body and includes an LCD or like device capable of indicating a variety of displays. The display unit 17 may be a special display device separate from the colorimeter main body. Indicated at 18 is an output unit for outputting data such as a color measurement result, temperature measurement result, and posture detection result to an external device such as a personal computer or printer. For example, if the output unit 18 is connected with the personal computer, the data such as the colorimetric value and temperature measurement value can be corrected or processed. Further, by connecting the output unit 18 with a general purpose robot and outputting the posture detection result, the posture adjustment can be performed using the general purpose robot. Indicated at 19 is a colorimetric optical system driver for driving the light projector unit 5 and the colorimetric optical system of the photosensor unit 6 in accordance with a control signal from the CPU 10.

Figure 6:
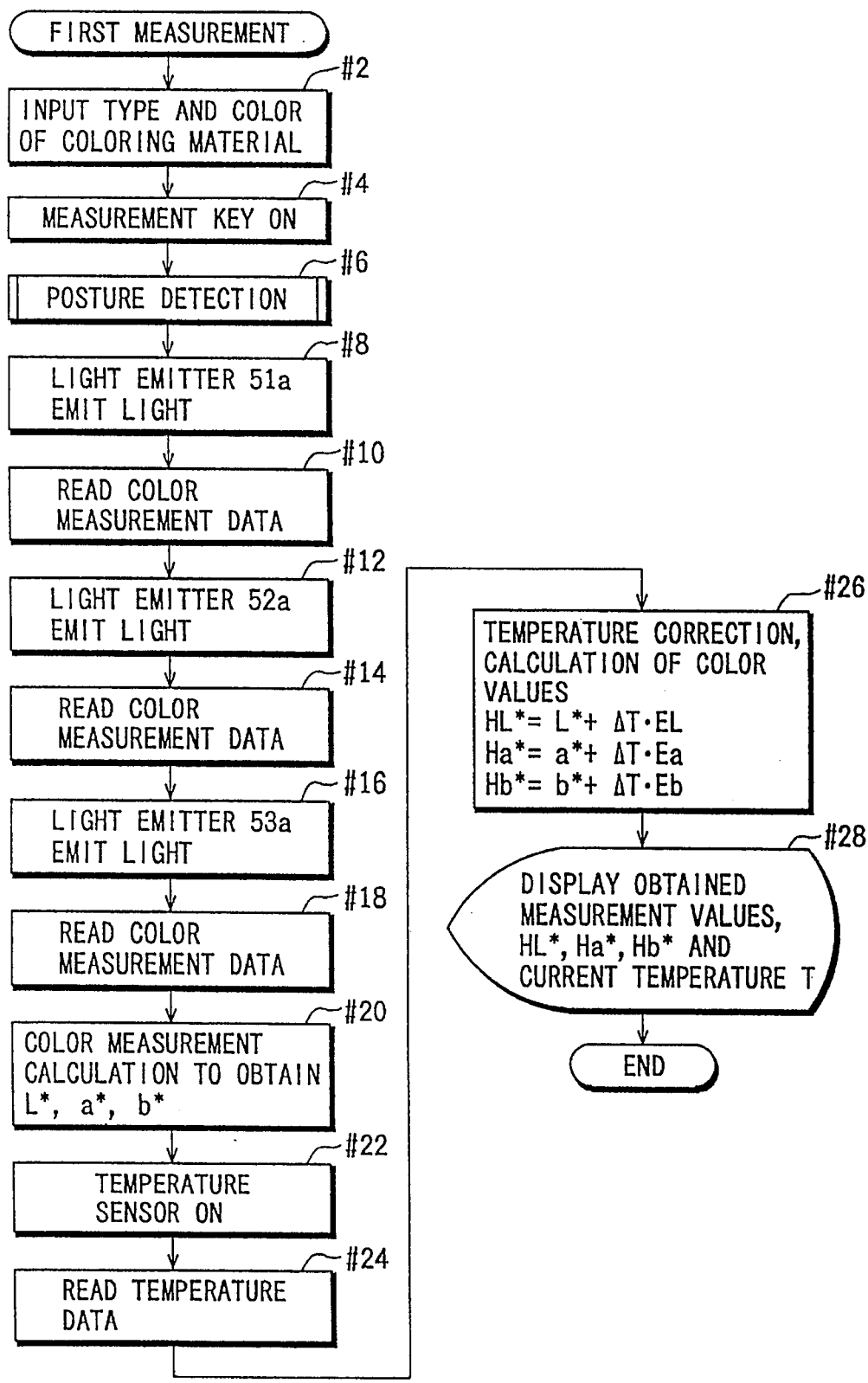
FIG. 6 is a flow chart showing a main routine of a first measurement ("Measurement I") of the first colorimeter.
Figure 7:
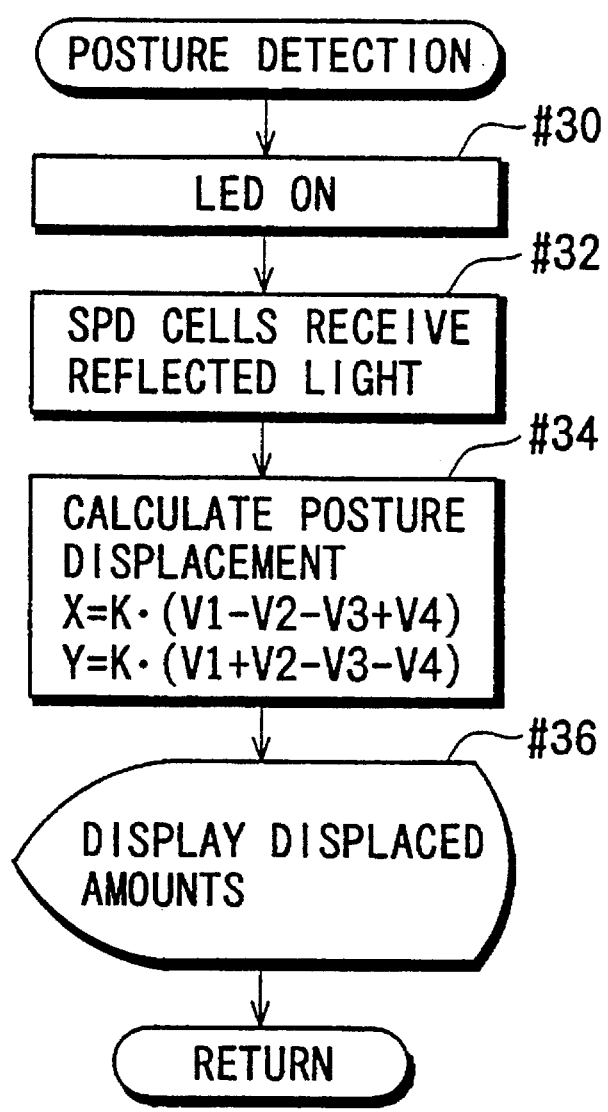
FIG. 7 is a flow chart showing a subroutine of a posture detection ("Posture Detection") carried out in the first measurement.
Figure 8:
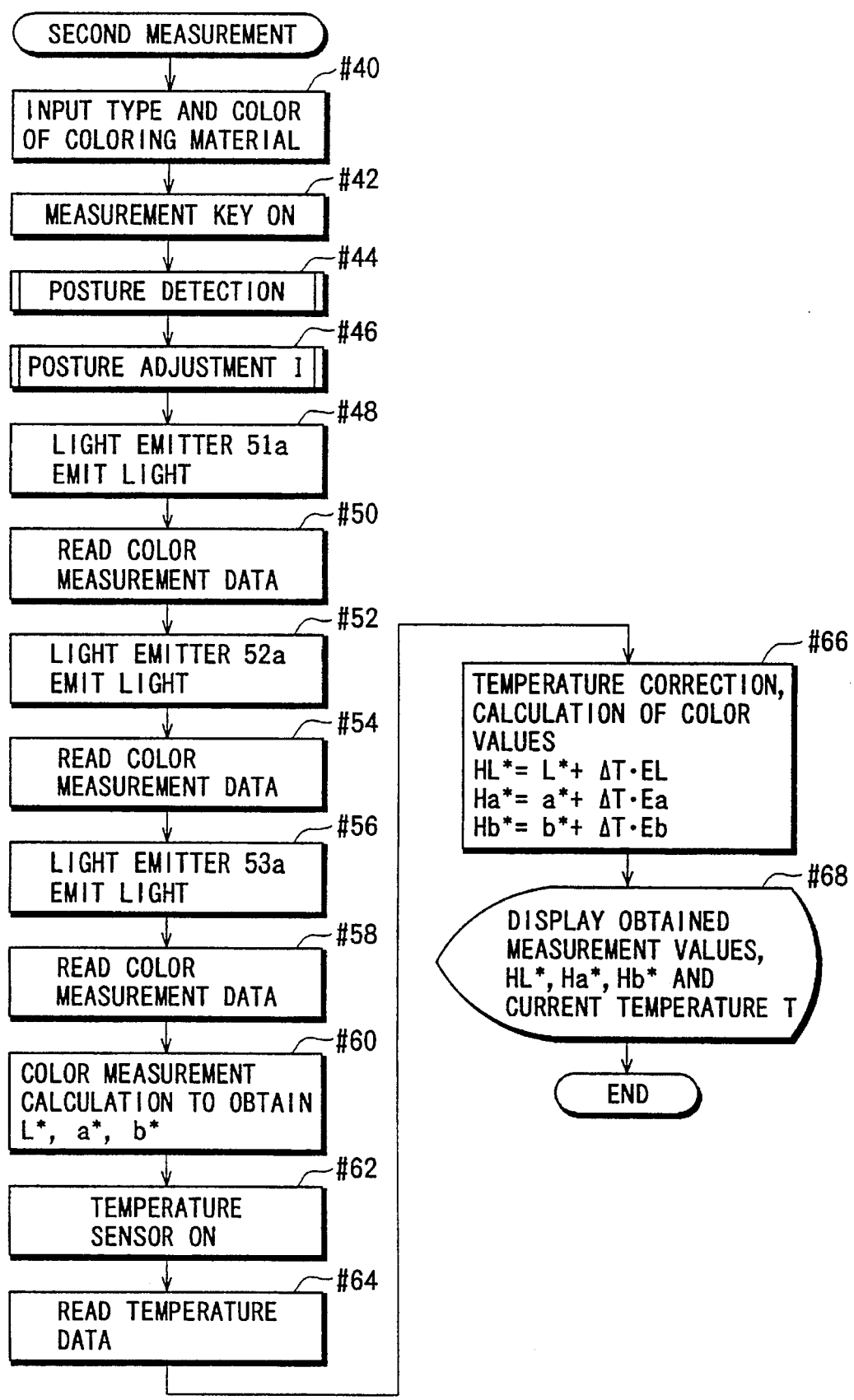
FIG. 8 is a flow chart showing a main routine of a second measurement ("Measurement II") of the first colorimeter.
Figure 9:
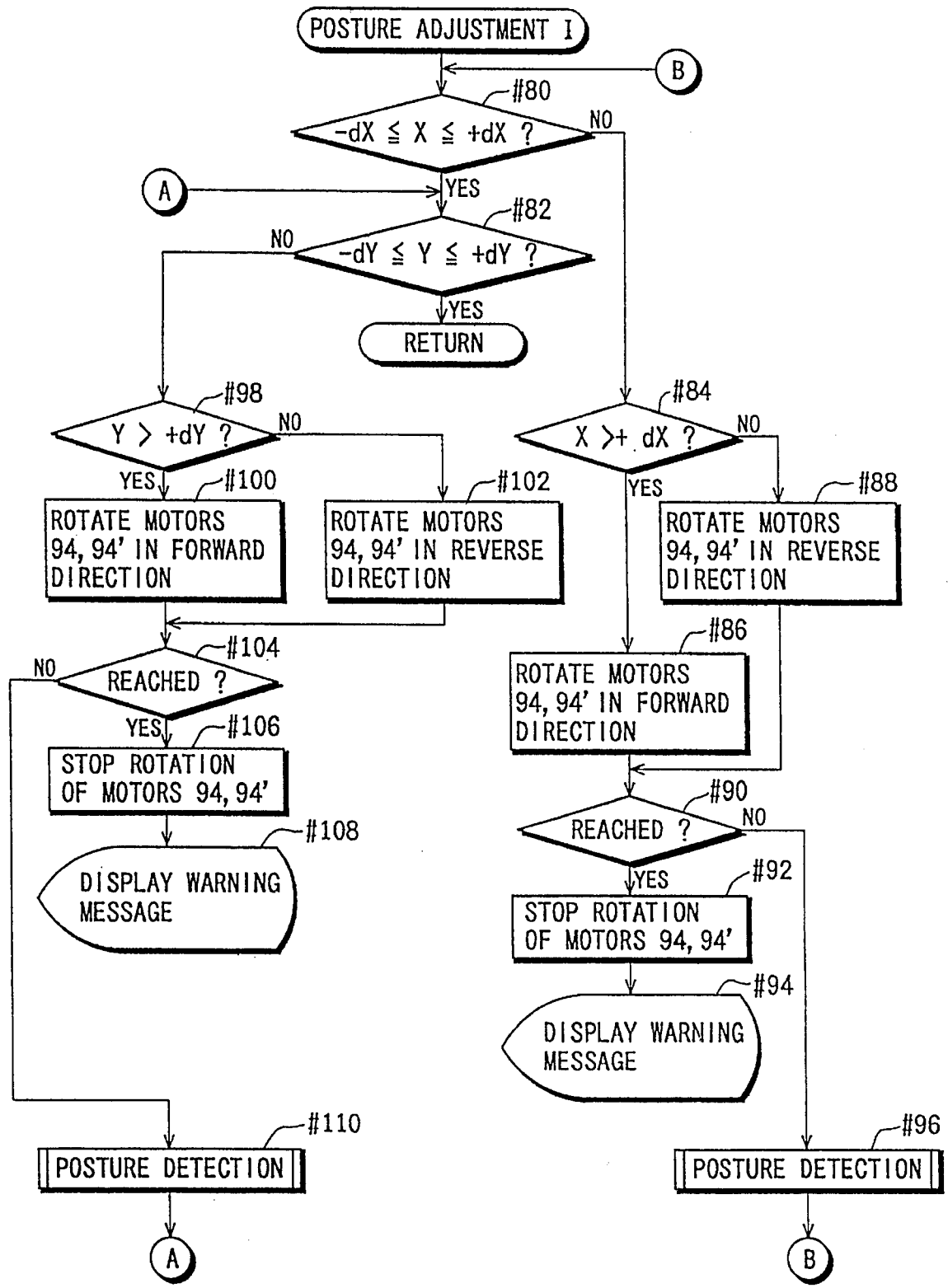
FIG. 9 is a flow chart showing a subroutine of a posture adjustment ("Posture Adjustment I") carried out in the second measurement.

FIGS. 6 to 9 are flow charts showing operations of the first colorimeter. FIGS. 6 and 7 show a first measurement, and FIGS. 8 and 9 show a second measurement.

The first measurement is carried out when the colorimeter includes the posture detector 8 and the display unit 7, but not the posture adjusting mechanism 9.

In FIG. 6, the type of the colorant and the color are first input so as to enable a temperature correction (Step #2). Then, a measurement key in the operation unit 12 is turned on (Step #4). The posture detection is made prior to the measurement (Step #6) when the measurement key is turned on.

A subroutine "Posture Detection" is described with reference to FIG. 7. First, the LED 81d is turned on (Step #30), and the reflected light from the surface of the object 4 is received by the respective cells of the SPD 82d (Step #32). The CPU 10 calculates a posture displacement (a difference between the reference posture (vertical) and the current posture (inclination)) in accordance with the data from the respective cells (Step #34). More specifically, a displaced amount X on the X-plane is calculated: $X=K(V1-V2 V3+V4)$ and a displaced amount on the Y-plane is calculated: $Y=K(V1+V2-V3-V4)$. Parameters V1 to V4 used in these calculations are corrected using the aforementioned correction factors K1 to K4. Further, K denotes a conversion efficient used to convert a voltage value into a measurement value or an angle.

The displaced amounts obtained as a result of the calculation are displayed in the display unit 17 (Step #36). An operator adjusts the posture based on the displayed displaced amounts and tries to accurately keep the displaced amounts within their permissible range or, preferably, make them zero by repeating the posture adjustment and the posture detection thereafter. Another construction for manually adjusting the posture may be such that a circular operation dial or the like a circumferential surface of which is partially projecting from the colorimeter main body is mounted in place of the motors 94 and 94' of FIG. 4. The projecting distances of the support legs 96 and 96' can be adjusted by turning this operation dial clockwise or counterclockwise. The posture adjusting mechanism 9 of FIG. 4 does not necessarily have to be manually operable. Any suitable methods may be adopted to adjust the posture. For example, the posture of the colorimeter main body may be adjusted by putting a multitude of thin sheets below the support legs 96. The displacement can be corrected rapidly, easily and accurately because the posture adjustment can be made while confirming the displaced amounts being displayed.

In the normal colorimeter including one light projector and one photosensor, the light projector may automatically project light when the displaced amount becomes permissible while manually performing the posture adjustment, to conduct a color measurement. In the case of one light projector, light emission (measurement) time is instantaneous. Thus, even with this construction, data having sufficiently high reproducibility can be obtained and the measurement can be made rapidly and easily.

Figure 10:
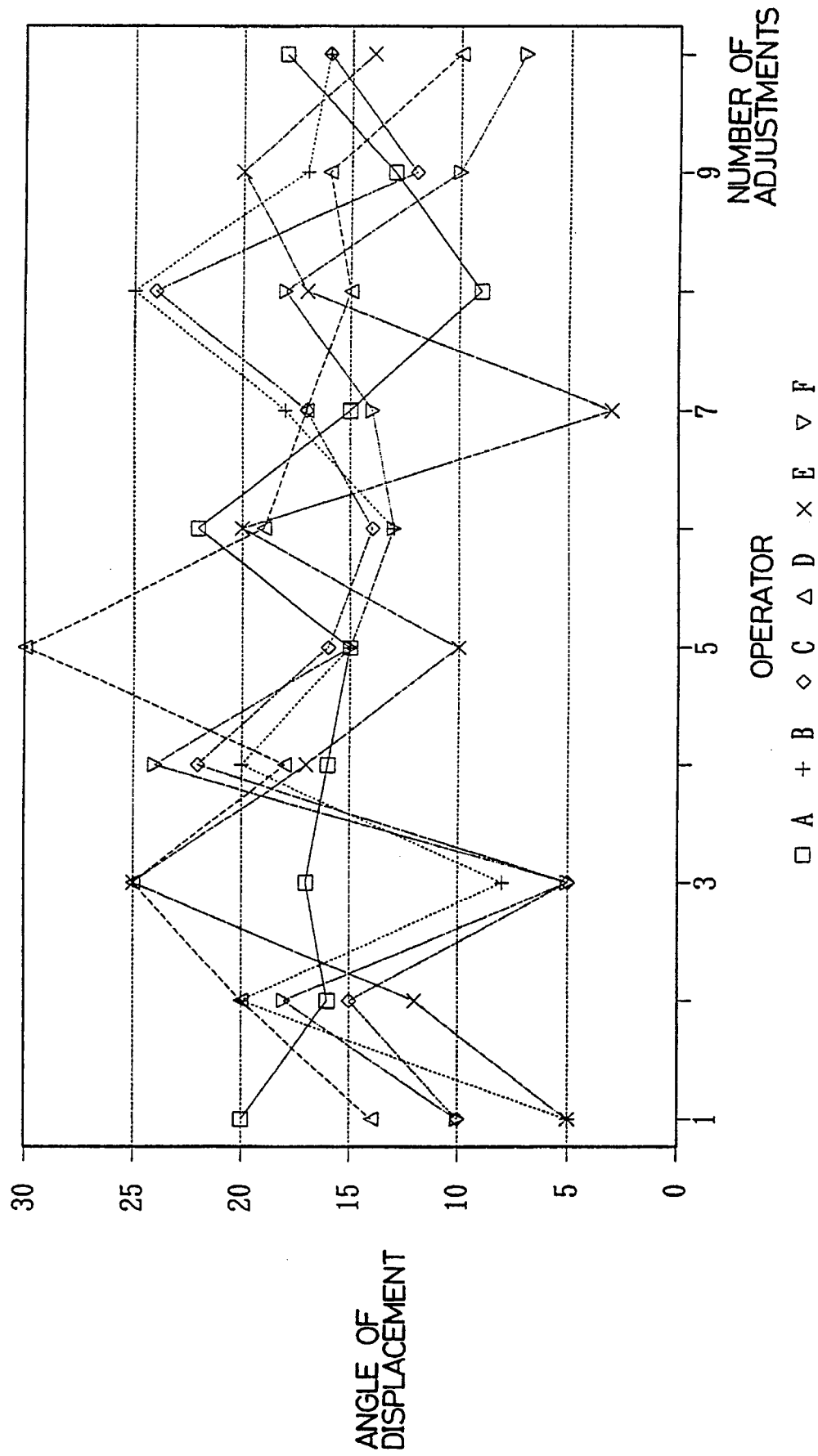
FIG. 10 is a graph showing a displacement from a reference posture when the posture of the apparatus main body is adjusted on the basis of an operator's judgment.

FIG. 10 shows experiment data representing displaced amounts from the reference posture when the posture is adjusted on the basis of the operators' feelings. FIG. 10 shows the posture adjustments performed by six persons A to F. A horizontal axis represents the number of adjustments and a vertical axis represents an angle of displacement from the reference posture (vertical posture). As seen from FIG. 10, the displacement is, on the average, 15 to 20 minutes and largely varies each time for each person. This shows low reproducibility of the measured color data.

Figure 11:
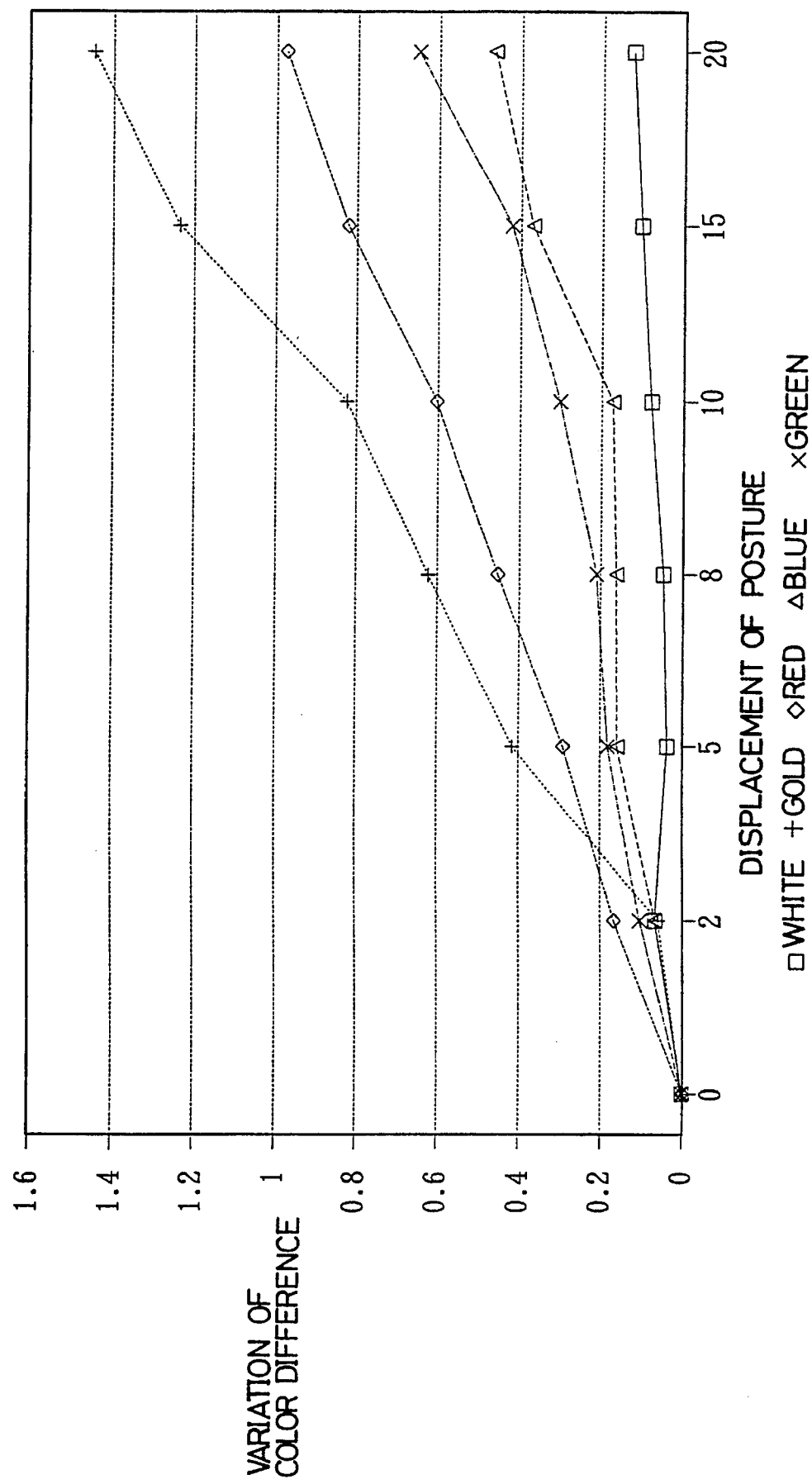
FIG. 11 is a graph showing a color difference variation in relation to the displacement of the apparatus main body from the reference posture.

FIG. 11 shows a color difference variation corresponding to a displacement of the colorimeter main body from its reference posture. Specifically. FIG. 11 shows a color difference variation for five colors: white, gold, red, blue and green (where white is painted on a solid plate and the other colors are painted on metallic plates). A horizontal axis represents a displacement of the posture and a vertical axis represents a variation $\Delta E^*ab$ of color difference. As described above, since the average displacement is 15 to 20 minutes in FIG. 10, a color difference variation is greater than 1 in the case of gold and close to 1 in the case of red. On the other hand, in view of TABLE-1. this color difference variation corresponds to a temperature change of 10° C. or more. Thus, it can be understood that an error in inclination of the colorimeter main body causes a large error in a color measurement result.

Referring back to FIG. 6, the light sources 51a to 53a are caused to emit light one after another and, each time, the reflected light is received by the photosensor unit 6 and the color measurement data is read (Steps #8 to #18). Subsequently, the color measurement calculations are performed to obtain L*, a*, and b* (Step #20). Thereafter, the thermopile 72 as a temperature sensor is turned on and the temperature data is read (Steps #22 and #24). Using this temperature data and the temperature correction data stored in the memory 11, color values HL*, Ha*, and Hb* after the temperature correction are calculated in accordance with the following Equations (1) to (3).

$$HL^* = L^* + \Delta T \times EL \tag{1}$$

$$Ha^* = a^* + \Delta T \times Ea \tag{2}$$

$$Hb^* = b^* + \Delta T \times Eb \tag{3}$$

where $\Delta T$ denotes a difference (°C.) from a reference temperature, EL, Ea, Eb are each a variation value per 1° C. The obtained measurement values HL*, Ha*, Hb* and a current temperature T are displayed in the display unit 17.

The operator can easily confirm whether or not the measurement was conducted while the colorimeter main body is displaced because the displaced amount of the posture is displayed in Step #36. Accordingly, if the displaced amount of the posture is beyond the permissible range, the posture adjustment is made while confirming the displayed displaced amount of the posture or memorizing the same and the color measurement is conducted again. Once the posture adjustment is made, it is not necessary to readjust the posture during a series of measurements.

Next, the second measurement is described. In the second measurement, the posture adjusting mechanisms 9 are utilized.

In the flow chart of FIG. 8, the type of the colorant and the color are first input to enable a temperature correction (Step #40). Then, a measurement key in the operation unit 12 is turned on (Step 42). The posture detection is made prior to the measurement (Step #44) when the measurement key is turned on. Since the subroutine "Posture Detection" is identical to the one of FIG. 7, no description is given here. Subsequently, a subroutine "Posture Adjustment I" is carried out (Step #46).

This subroutine "Posture Adjustment I" is described with reference to FIG. 9.

It is first judged whether the displaced amounts X and Y are within their permissible ranges, i.e., $-dX \leq x \leq dX$ and $-dY \leq Y \leq dX$ (Steps #80 and #82). This subroutine returns if the both displaced amounts are within their permissible range.

If the displaced amount X is beyond its permissible range, it is judged whether X>dX (Step #84). If X>dX (YES in Step #84), the motors 94 and 94' are rotated in the forward and reverse directions, respectively (Step #86). Conversely, if X<−dX (NO in Step #84), the motors 94 and 94' are rotated in the reverse and forward directions, respectively (Step #88).

At this stage, it is judged whether the engaged position of the threaded portion 961 with the gear 97 has reached one of the limits of the movable range of the threaded portion 961 (positions 2 millimeters away from its actual limits in this embodiment) in Step #90. If the judgment result is in the affirmative, the rotation of the motors 94 and 94' is stopped (Step #92) and a warning message is displayed (Step #94). If the limit has not been reached (NO in Step #90), the subroutine "Posture Detection" is carried out (Step #96). The displaced amount X is made permissible by repeating the posture detection and the posture adjustment in this way.

On the other hand, if the displaced amount Y is beyond its permissible range (NO in Step #82), it is judged whether Y>dY (Step #98). If Y>dY (YES in Step #98), the motors 94 and 94' are both rotated in the forward direction (Step #100). Conversely, if Y<−dY (NO in Step #98), the motors 94 and 94' are both rotated in the reverse direction (Step #102).

At this stage, it is judged whether the engaged position of the threaded portion 961 with the gear 97 has reached one of the limits of the movable range of the threaded portion 961

(Step #104). If the judgment result is in the affirmative, the rotation of the motors 94 and 94' is stopped (Step #106) and a warning message is displayed (Step #108). If the limit has not been reached (NO in Step #104), the subroutine "Posture Detection" is carried out (Step #110). The displaced amount Y is made permissible by repeating the posture detection and the posture adjustment in this way.

Next, a second colorimeter of the present invention will be described with reference to FIGS. 12 and 13.

Figure 12:
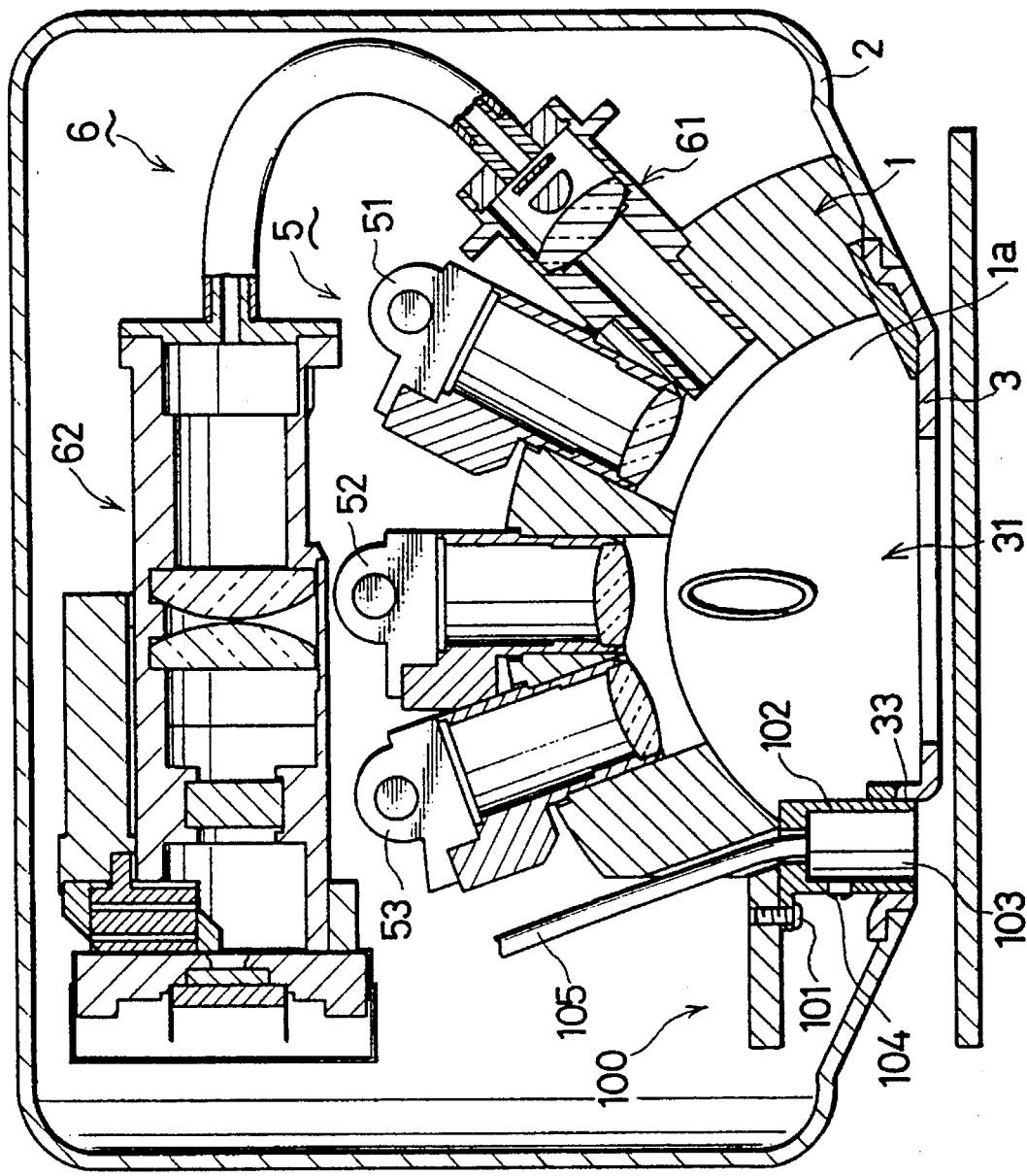
FIG. 12 is a front view in section showing a mechanical construction of a colorimeter as a second embodiment of the present invention.
Figure 13:
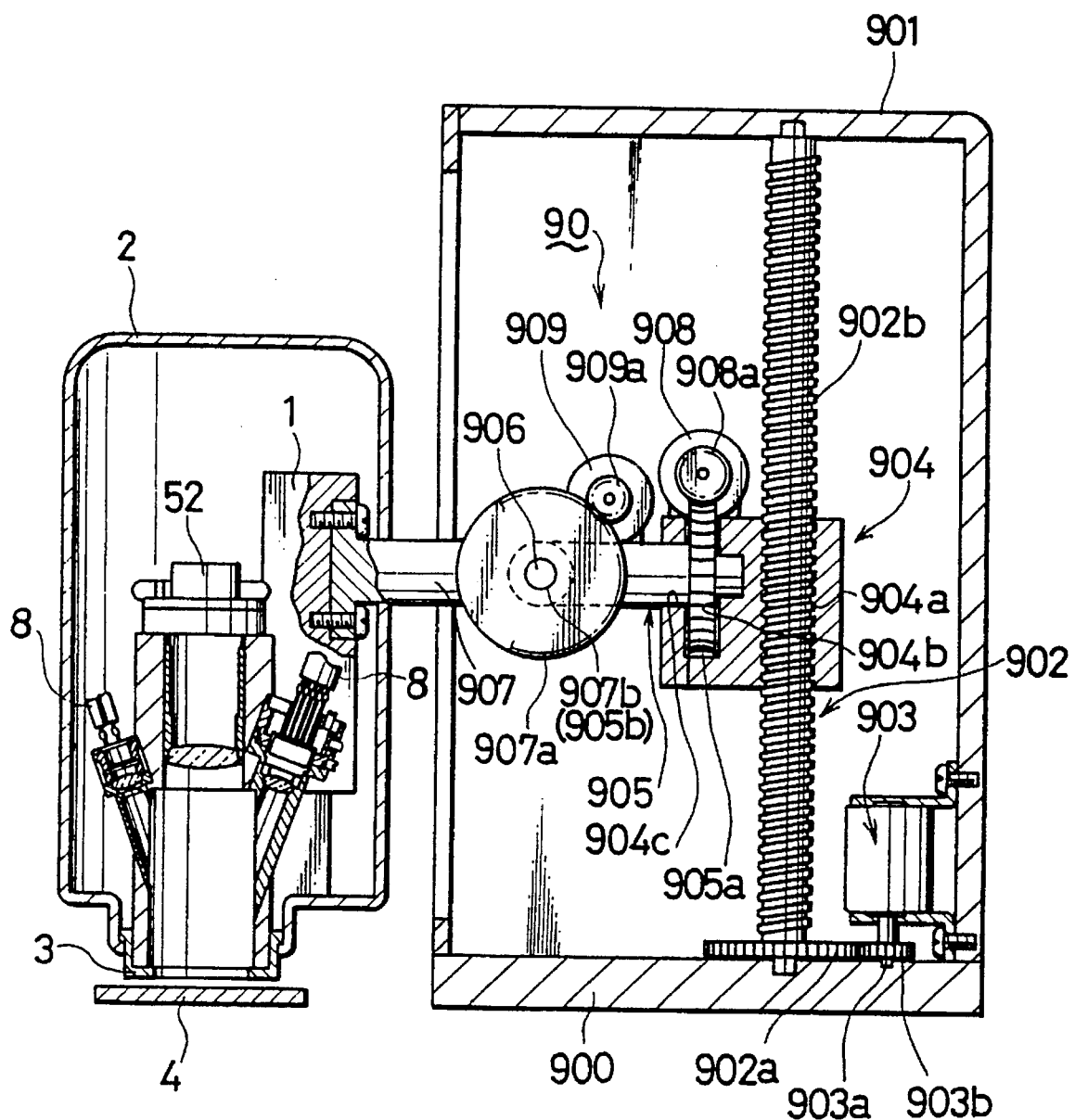
FIG. 13 is a side view in section showing a posture adjusting mechanism of the second colorimeter.

FIGS. 12 and 13 are a sectional front view and a sectional side of the second colorimeter. In these figures, elements identified with the same reference numerals as those in the first embodiment have the same functions.

The second colorimeter differs from the first colorimeter in that the colorimeter main body is not brought into contact with an object. Accordingly, the projection 32 shown in FIG. 1 is not particularly formed around the periphery of the opening 31 of the foot member 3, making the foot member 3 flat.

A distance detector 100 is mounted on an optical base member 1 by means of a screw 101, and a leading end thereof is fitted in a hole 33 of a specified diameter formed in a specified position of a downward facing surface of the foot member 3, so that the leading end of the distance detector 100 faces the surface of an object 4 to be measured. The distance detector 100 includes a hollow cylindrical holder 102 fitted into the hole 33 of the foot member 3, a displacement sensor 103 of overcurrent type which is fitted into the holder 102, a coupling screw 104 for securing the sensor 103 with the holder 102 and a lead wire 105 for sending a detection signal.

The displacement sensor 103 includes a magnetic flux generation coil and a detection coil on a horizontal surface. The sensor 103 alternating current to flow through the magnetic flux generation coil in a state where it faces the surface of the object 4 and detects a level of a current generated in the detection coil. More specifically, the sensor 103 generates an alternating magnetic flux which is normal to the surface of the object by causing the alternating current to flow through the magnetic flux generation coil. This alternating magnetic flux causes a flow of overcurrent on the object surface. The detection coil receives a magnetic flux generated by this overcurrent to detect an induced current. Consequently, the sensor 103 is capable of detecting a current of a level corresponding to a distance between the object surface and the detection. The distance detector 100 may include a mechanical sensor in place of an optical or magnetic sensor of non-contact type.

A posture adjusting mechanism 90 is shown in detail in FIG. 13. This mechanism 90 is connected as a separate element with the colorimeter main body, behind a housing 2. The mechanism 90 is connected by way of the optical base member 1 and includes a base plate 900 and a housing 901. An adjusting mechanism is disposed in a space defined by the base plate 900 and the housing 901.

Indicated at 902 a distance adjusting shaft which rotatably stands between the base plate 900 and the housing 901. A gear 902a having a specified diameter fixedly attached on a bottom end of the shaft 902. A threaded portion 902b is formed in an entire periphery of the shaft 902. A motor 903 is secured at a lower end position of a rear part of the housing 901 by means of a screw or like coupling member with faced downward. A gear 903b engageable with the gear 902a is integrally mounted on a rotatable shaft 903a of the motor 903. A bottom end of the rotatable shaft 903a is fitted with the base plate 900 to support the shaft 903a.

Indicated at 904 is a movable block. A threaded hole 904 is formed in the block 904. The threaded hole 904 is in engagement with the threaded portion 902b of the shaft 902. An unillustrated upstanding guide member restricts the block 904 from rotating with the rotation of the shaft 902, so that the block 904 is movable only along the length of the shaft 902. Further, in the block 904 is formed a hole 904b having a large diameter and a hole 904c having a small diameter. The large hole 904b and the small hole 904c are coaxially arranged.

Indicated at 905 is a first arm in the form of a cylindrical shaft. The first arm 905 is fixedly attached with a worm wheel 905a on a free end thereof. The first arm 905 is rotatably fitted in the small hole 904c of the block 904 while the worm wheel 905a is rotatably disposed in the large hole 904b.

In the other end of the first arm 905 is formed a hole 905b extending perpendicularly to a longitudinal axis of the first arm 905. A coupling shaft 906 is rotatably fitted in the hole 905b.

A second arm 907 is secured at the rear part of the optical base member 1 by means of screws, bolts and nuts, or like fixing members, and projects and extends from the housing 2 toward the block 904. On a free end of the second arm 907 is formed a gear 907a having a specified diameter. The gear 907a is in parallel with a plane intersecting the shaft 902 and the first arm 905. A hole 907b is formed in the center of the gear 907a. The coupling shaft 906 is fixedly fitted in the hole 907b. Accordingly, the gear 907a or the second arm 907 is rotatable about the hole 905b formed in the first arm 905.

Indicated at 908 is an X-plane motor which is secured on a top of the movable block 904. The X-plane motor 908 is fixedly attached with a worm gear 908a engageable with the worm wheel 905a. Indicated at 909 is a Y-plane motor which is carried by the first arm 905. A gear 909a engageable with the gear 907a is mounted on a rotatable shaft of the motor 909.

Although the temperature detector 7 is not illustrated in FIG. 12, it may be mounted, as shown in FIG. 1, in a position where it is symmetrical with the distance detector 100 with respect to the center of the opening 31. Alternatively, a temperature detector may be a portable separate device which is connected with the colorimeter main body by way of a flexible signal line, so that the temperature of the object 4 can suitably be measured. In the case where temperature correction is not particularly necessary such as when the measurement is conducted in a temperature-controlled working atmosphere or a colorant has a negligible temperature characteristic, the temperature detector 7 may not be provided. This is the same as in the first embodiment.

With the thus constructed colorimeter, when the motor 903 rotates, its rotational force is transmitted to the shaft 902 by way of the gears 903a and 902b, thereby moving the block 904 upward or downward. As the block 904 moves upward or downward. The first and second arms 905 and 907 integrally move upward or downward, thereby moving the colorimeter main body toward or away from the object 4.

The colorimeter main body moves upward when the motor 903 is driven in the forward direction, while moving downward when the motor 903 is driven in the reverse direction. Upon rotation of the X-plane motor 908, its rotational force is transmitted to the coupling shaft 906 by way of the worm gear 908a and the worm wheel 905a, thereby causing the second arm 907 to rotate about its axial center. In this way, the inclination of the colorimeter main body with respect to the object 4 on the X-plane is changed. Upon rotation of the Y-plane motor 909, its rotational force is transmitted to the gears 909a and 907a, thereby causing the second arm 907 to rotate about the coupling shaft 906.

In this way, the inclination of the colorimeter main body with respect to the object 4 on the Y-plane is changed.

Figure 14:
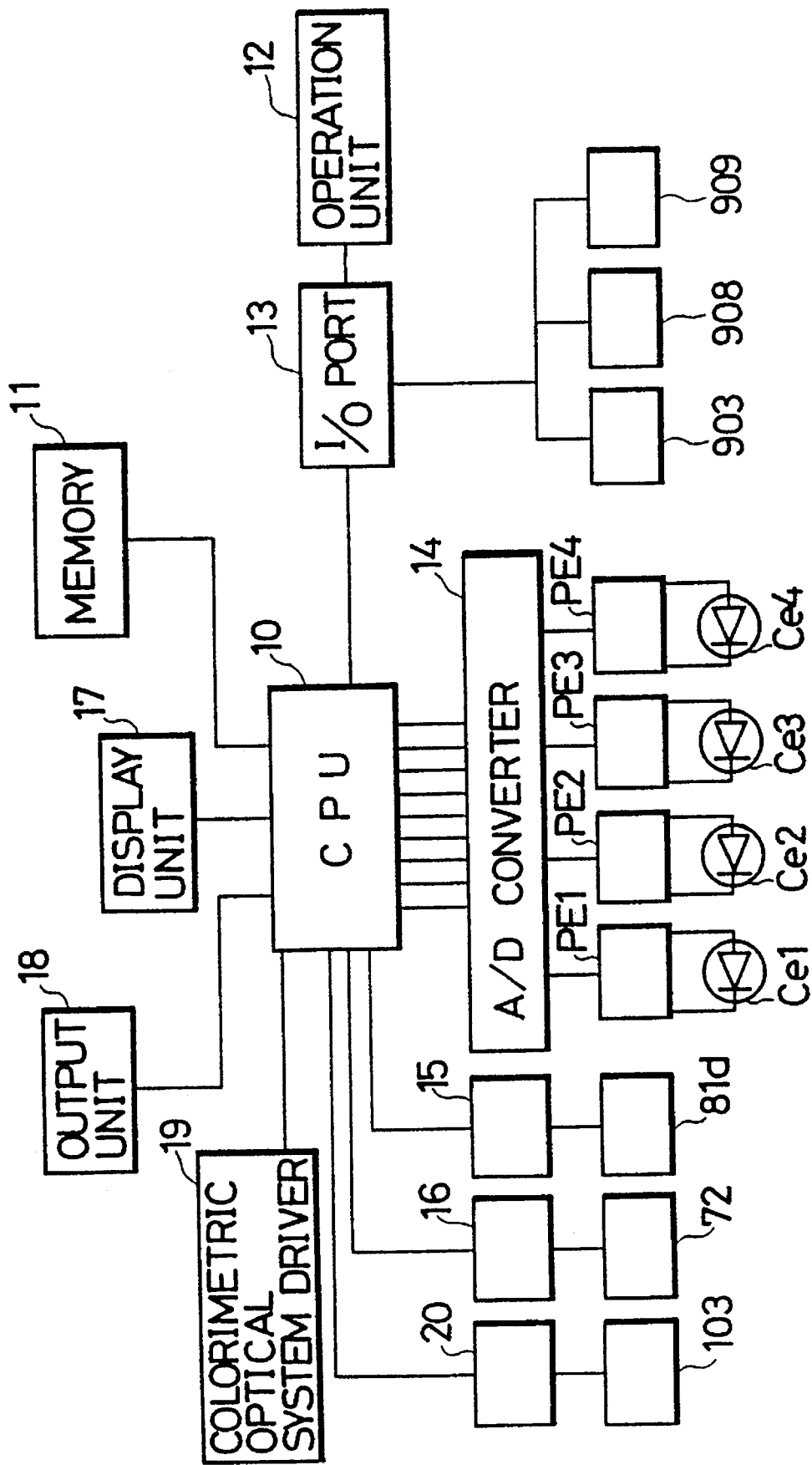
FIG. 14 is a circuit block diagram showing an electrical construction of the second colorimeter.

FIG. 14 is a circuit block diagram shown in an electrical construction of the second colorimeter. It will be noted that elements identified by the same reference numerals as those shown in FIG. 5 have the same functions.

Indicated at 20 is a signal processor for driving the distance detecting sensor 103 in accordance with a control signal from the CPU 10, converting and outputting a detection signal based on a specified linearity. An I/O port 13 is adapted to introduce the control data from the CPU 10 to the respective motors 903, 908 and 909.

FIGS. 15 to 18 are flow charts showing operations of the second colorimeter.

Figure 15:
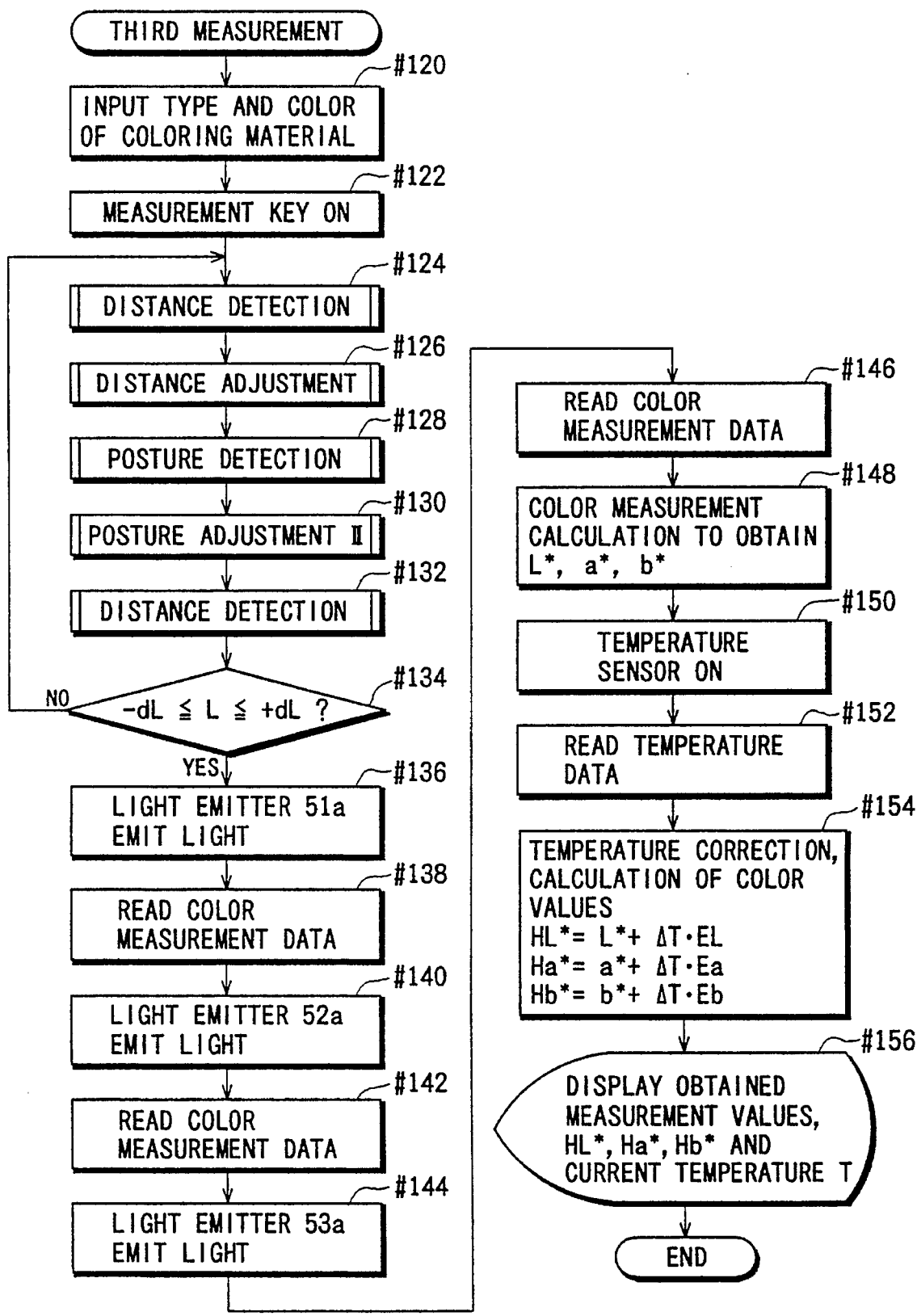
FIG. 15 is a flow chart showing a main routine of a measurement ("Measurement III") of the second colorimeter.

In FIG. 15, the type and color of the colorant are first input to enable a temperature correction (Step #120). Thereafter, when the measurement key is turned on (Step #122), the distance detection and distance adjustment and the posture detection and posture adjustment and the distance detection are made (Steps #124 to #132). The color measurement is started if the distance and the posture are both permissible and the obtained color measurement result is displayed in the display unit 17 (YES in Step #134 and Steps #136 to #156). Here, no description is given on the operations carried out in Steps #136 to #156 as they are identical to those carried out in Steps #8 to #28 of FIG. 6 of the first embodiment.

Figure 16:
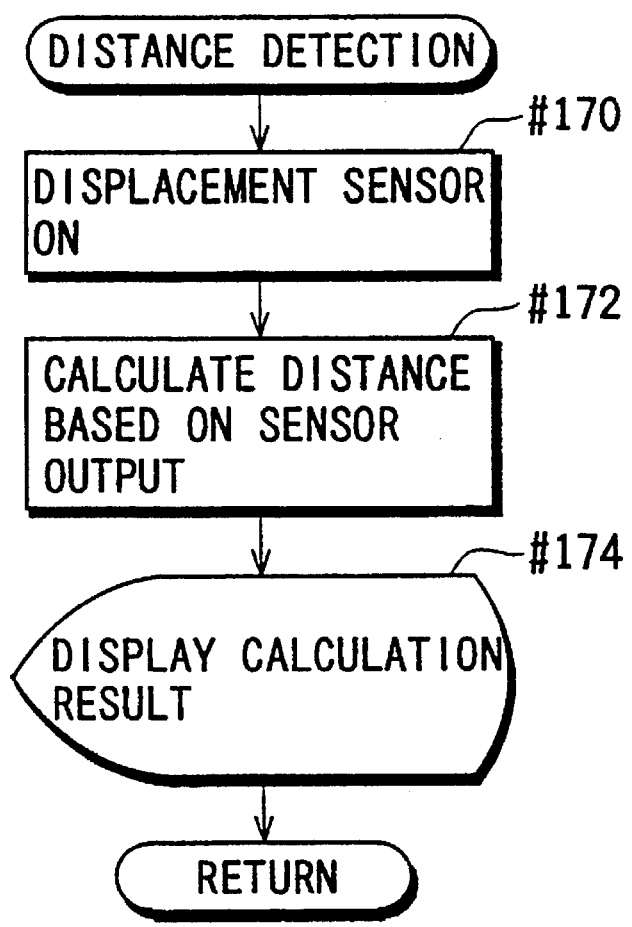
FIG. 16 is a flow chart showing a subroutine of a distance detection ("Distance Detection") carried out in the measurement of the second colorimeter.

FIG. 16 is a flow chart showing a subroutine "Distance Detection" carried in the main routine shown in FIG. 15.

First, the displacement sensor 103 is turned on (Step #170) and its output is read. The distance is calculated based on this sensor output (Step #172) and the calculation result is displayed in the display unit 17 (Step #174).

Figure 17:
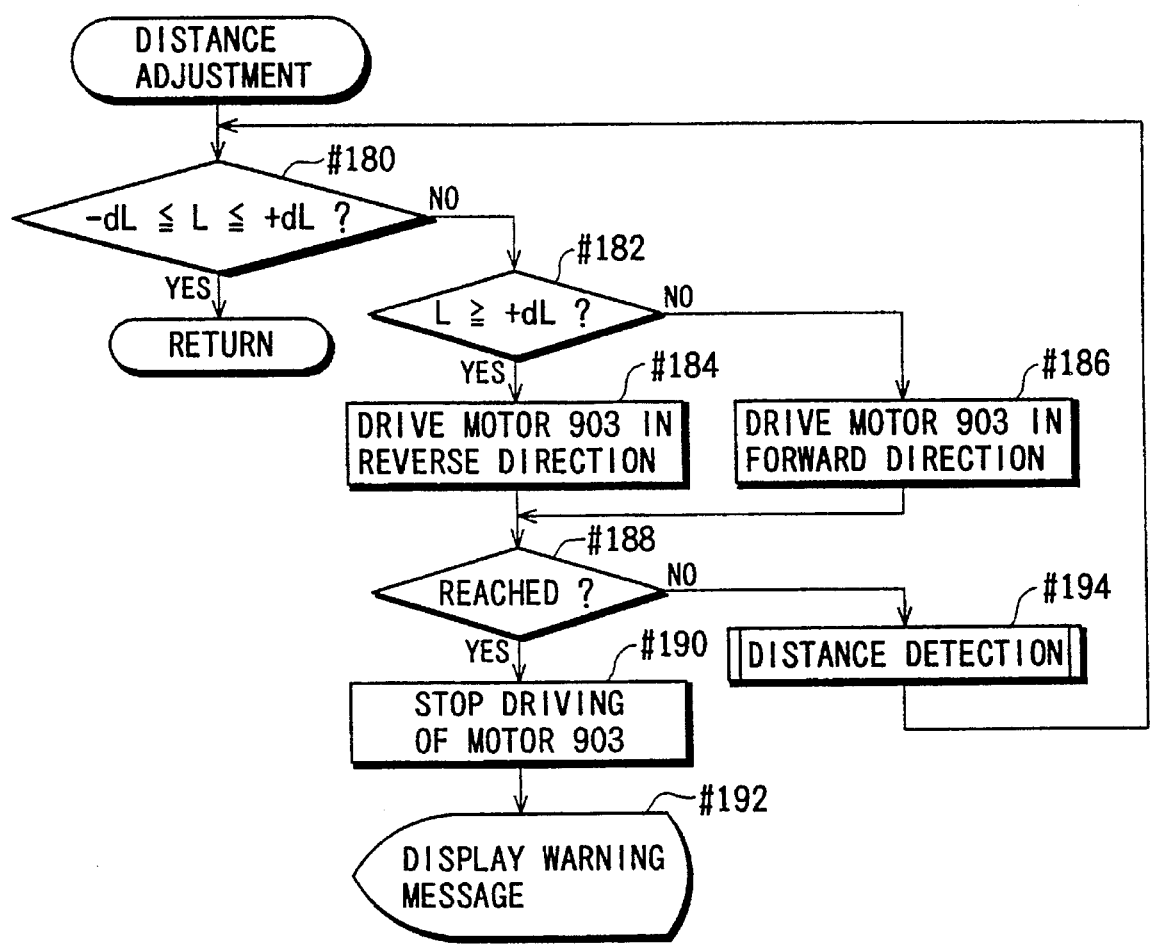
FIG. 17 is a flow chart showing a subroutine of a distance adjustment ("Distance Adjustment") carried out in the measurement of the second colorimeter.

FIG. 17 is a flow chart showing a subroutine "Distance Adjustment" carried in the main routine shown in FIG. 15.

It is first judged whether a current distance L obtained in Step #172 lies within its permissible range, i.e., $-dL \leq L \leq dL$ (Step #180). This subroutine returns if the current distance L lies within its permissible range (YES in Step #180).

If the current distance L lies beyond its permissible range (NO in Step #180), it is judged whether $L \geq dL$ (Step #182). If $L \geq dL$ (YES in Step #182), the motor 903 is driven in the reverse direction, thereby moving the colorimeter main body downward (Step #184). Conversely, if $L>-dL$ (NO in Step #182), the motor 903 is driven in the forward direction, thereby moving the colorimeter main body upward (Step #186). At this stage, it is judged whether the engaged position of the block 904 with the shaft 902 has reached an upper or lower limit of a movable range of the shaft 902 (Step #188). If the judgment result is in the affirmative (YES in Step #188), the driving of the motor 903 is stopped and a warning message is displayed (Steps #190 and #192). If the judgment result is in the negative (NO in Step #188), the subroutine "Distance Detection" is carried out (Step #194). The current distance L is made to lie within its permissible range centering a specified reference distance by repeating the distance detection and the distance adjustment in this way.

Upon completion of the distance detection and the distance adjustment (Steps #124 and #126), the posture detection and the posture adjustment are made (Steps #128 and #130). No description is given on the posture detection because it is identical to the one shown in FIG. 7.

Figure 18:
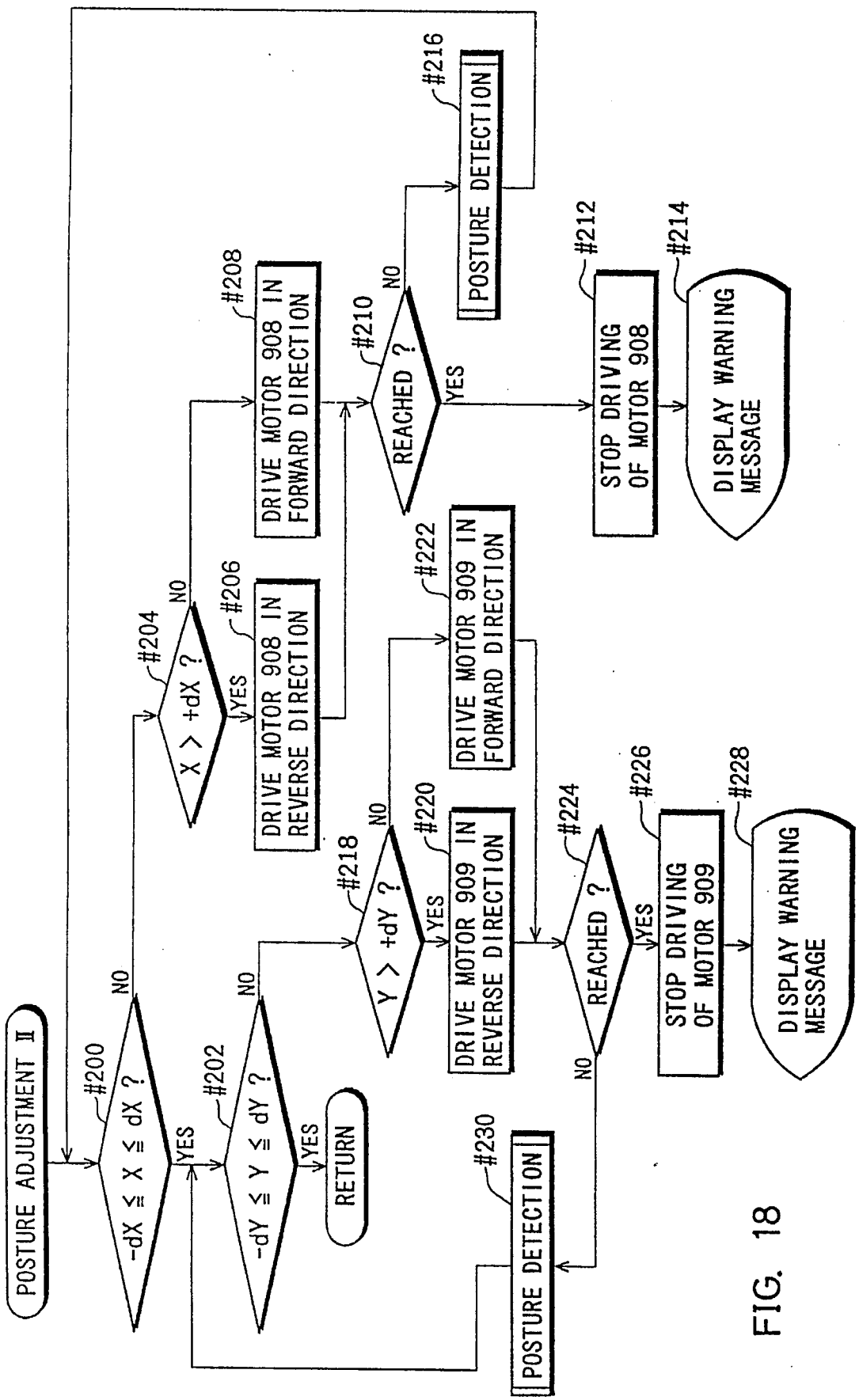
FIG. 18 is a flow chart showing a subroutine of a posture adjustment ("Posture Adjustment II") carried out in the measurement of the second colorimeter.

FIG. 18 is a flow chart showing a subroutine "Posture Adjustment II" carried out in the main routine shown in FIG. 15.

It is first judged whether the displaced amounts X and Y lie within their permissible ranges $-dX \leq dX$, $-dY \leq dX$ (Steps #200 and #202). This subroutine returns if the both displaced amounts lie within their permissible ranges.

If the displaced amount X lies beyond its permissible range (NO in Step #200), it is judged whether X>dX (YES in Step #204), the motor 908 is driven in the reverse direction (Step #206). Conversely, if $X \leq -dX$ (NO in Step #204), the motor 908 is driven in the forward direction (Step #208). In this way, control is executed to move the colorimeter main body in such a direction as to approximate the displaced amount X to 0. At this stage, it is judged whether the engaged position of the worm wheel 905a with the worm gear 908a has reached a limit thereof (a specified rotational limit value of the colorimeter main body on the X-plane) (Step #210). If the judgment result is in the affirmative (YES in Step #210), the driving of the motor 908 is stopped and a warning message is displayed (Steps #212 and #214). If the judgment is in the negative (NO in Step #210), the subroutine "Posture Detection" is carried out (Step #216). The displaced amount X is made to lie within its permissible range by repeating the "Posture Detection" and the "Posture adjustment II" in this way.

If the displaced amount Y lies beyond its permissible range (NO in Step #202), it is judged whether Y>dY (Step #218). If Y>dY (YES in Step #218), the motor 909 is driven in the reverse direction (Step #220). Conversely, if $Y \leq -dY$ (NO in Step #218), the motor 909 is driven in the forward direction (Step #222). At this stage, it is judged whether the engaged position of the gear 907a with the gear 909a has reached a limit thereof (opposite ends of the gear, or a specified rotational limit value of the colorimeter main body on the Y-plane) (Step #224). If the judgment result is in the affirmative (YES in Step #224), the driving of the motor 909 is stopped and a warning message is displayed (Steps #226 and #228). If the judgment result is in the negative (NO in Step #230), the subroutine "Posture Detection" is carried out (Step #230). The displaced amount Y is made to lie within its permissible range by repeating the "Posture Detection" and the "Posture Adjustment II" in this way.

Upon completion of the "Posture Detection" and the "Posture Adjustment II", the distance detection is made again (Step #132). This takes care of a case where the distance between the colorimeter main body and the object 4 changes by moving the colorimeter main body on the X- and Y-planes during the "Posture Adjustment" of Step #130 after the distance is adjusted in Step #126. If the obtained current distance L lies within its permissible range (YES in Step #134), the color measurement is conducted as described above. The operations of Steps #124 to #132 are repeated if the detection result lies beyond the permissible range.

Figure 19:
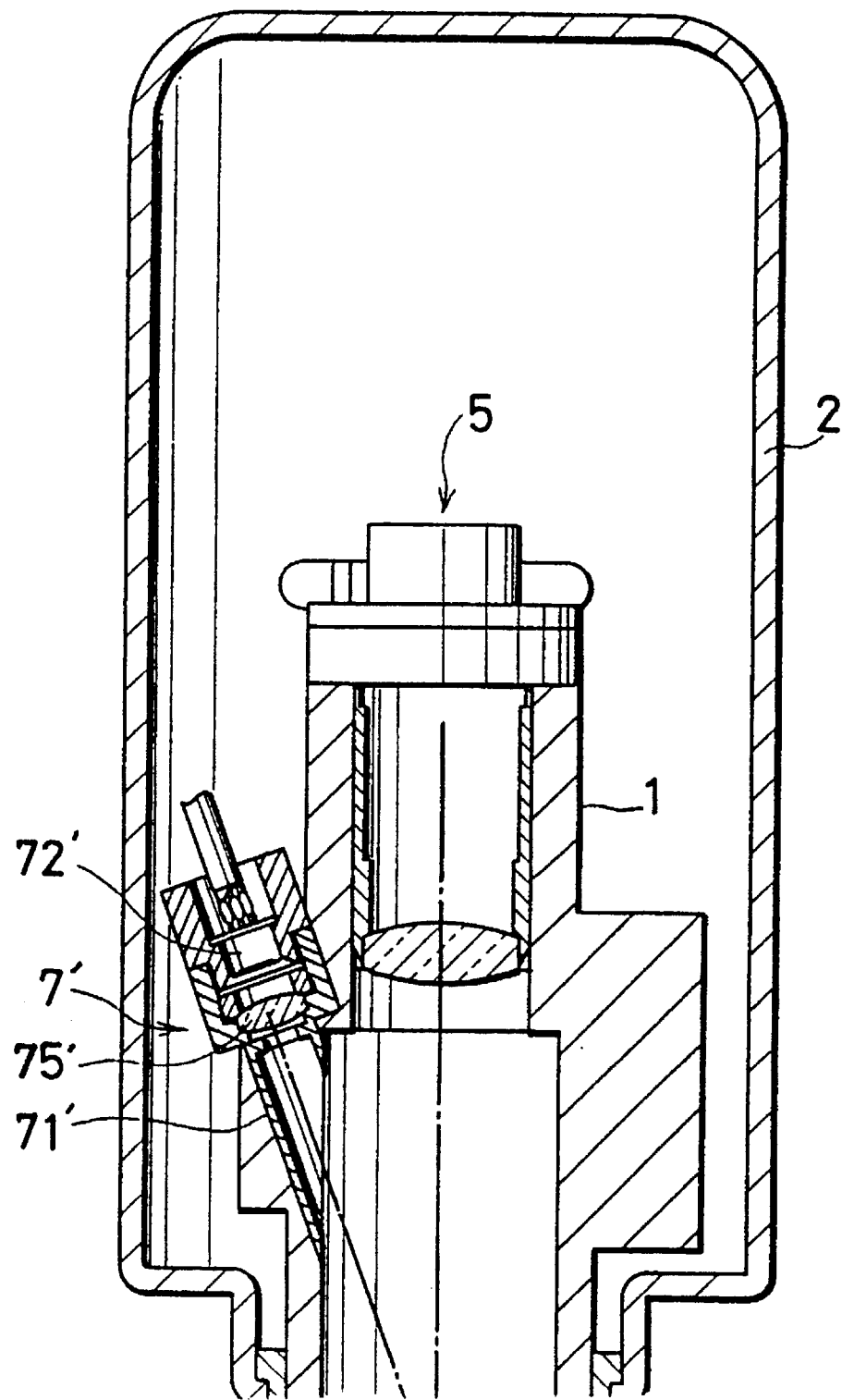
FIG. 19 is a side view in section showing a construction of a temperature detector of the second colorimeter.

FIG. 19 is a side view in section showing a temperature detector of the second colorimeter.

A temperature detector 7' is mounted on the optical base member 1 which is similar to the first embodiment. However, in this embodiment, the temperature detector 7' is mounted in the optical base member 1 facing the measurement space 1a. In this case, the posture detector 8 is disposed in a different position. Disposition of a condenser lens 75' before a thermopile 72' realizes measurement accuracy of specified level even if a distance between the colorimeter main body and the object 4 becomes longer. By adjusting an optical axis of the thermopile 72' and the condenser lens 75' to the center of the opening 31 and extending the free end of a holder 71 along this optical axis up to the measurement space 1a. a temperature measurement can be conducted at the same position of the object 4 as a color measurement. It should be noted that this arrangement of a temperature detector 7' can be applied to the first embodiment.

Unless a temperature correction is applied to the color measurement value, the operations of Steps of #2 and #26 (and Steps #40 and #66, #120 and #154 corresponding thereto) are unnecessary during the color measurement. In this case, only the measured current temperature T may be displayed, or the temperature measurement may be even omitted and therefore no temperature display is made.

Figure 20:
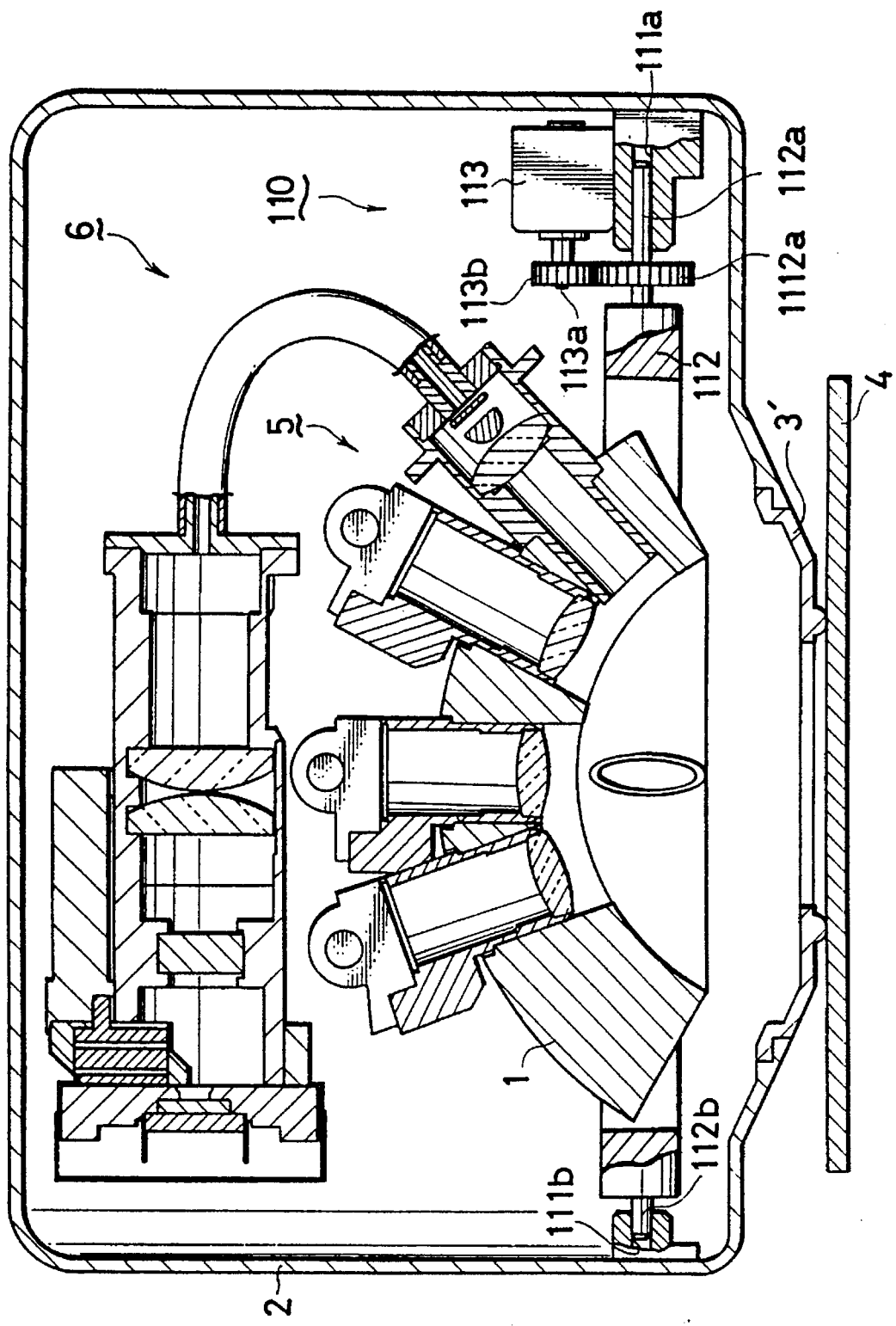
FIG. 20 is a front view in section showing a mechanical construction of a colorimeter as a third embodiment of the present invention.
Figure 21:
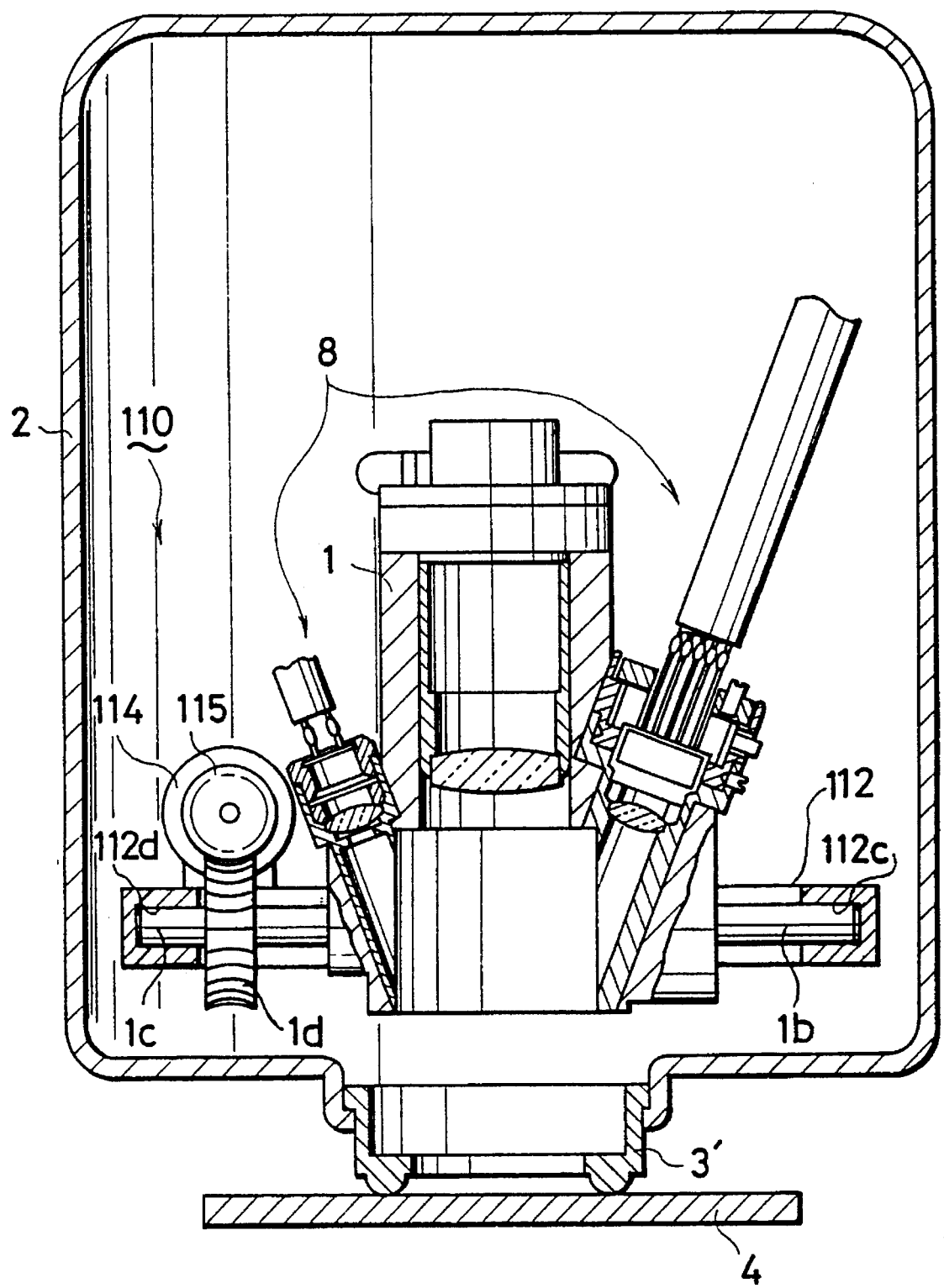
FIG. 21 is a side view in section showing a posture adjusting mechanism of the third colorimeter.

FIGS. 20, 21, 23A and 23B show a construction of a colorimeter as a third embodiment of the present invention. FIGS. 20 and 21 are a sectional front view and a sectional side view of the third colorimeter, respectively. It should be appreciated that elements identified by the same reference numerals as those in the first and second embodiments have the same functions. Although unillustrated, a temperature detector 7 is disposed in a specified position similar to the first embodiment.

The third embodiment employs a posture adjusting mechanism 110 in place of the posture adjusting mechanisms 9 of the first embodiment. Specifically, in the first embodiment, the optical base member 1 is securely accommodated in the housing 2 and the posture adjusting mechanisms 9 drive the optical base member 1 and the housing 2 integrally to make a posture adjustment. In the third embodiment, the optical base member 1 is movably accommodated in the housing 2 and the posture adjusting mechanism 110 drives only the optical base member 1 to make a posture adjustment (at this stage, the housing 2 is in a fixed position relative to the object 4). Hereafter, the third embodiment is described.

As shown in FIG. 20, a support plate member 112 is integrally attached with shafts 112a and 112b extending outwards on the X-plane or along a line perpendicularly intersecting the Y-plane. Also, as shown in FIG. 21, the support plate member 112 is formed with holes 112c and 112d which are oppositely arranged on a line perpendicularly intersecting the X-plane.

The shafts 112a and 112b are rotatably fitted in bearings 111a and 111b, respectively. The bearings 111a and 111b is fixedly attached on an inner surface of the housing 2.

A Y-plane motor 113 is secured on a top of the bearing 111a by means of an unillustrated fixing device, and a gear 113b is mounted on a rotatable shaft 113a of the Y-plane motor 113. The gear 113b is in engagement with a gear 1112a mounted on the shaft 112a. In this construction, when the Y-plane motor 113 rotates, its rotational force is transmitted to the shaft 112a by way of the gears 113b and 1112a, thereby rotating the support plate member 112 about the shafts 112a and 112b. In other words, the support plate member 112 is rotatable with respect to the Y-plane.

The optical base member 1 is integrally attached with shafts 1b and 1c. These shafts 1b and 1c extend along the same line as the holes 112c and 112d formed in the support plate member 112. These shafts 1b and 1c are rotatably fitted in the holes 112c and 112d, respectively. In this way, the optical base member 1 is rotatable about the shafts 1b and 1c with respect to the X-plane. Further, a worm gear 1d is fixedly attached on the shaft 1c of the optical base member 1.

An X-plane motor 114 is secured on the support plate member 112 by means of an unillustrated fixing device. On a rotatable shaft 114a of the motor 114 is mounted a worm gear 115 which is in engagement with the worm wheel 1d attached on the shaft 1c. In this construction, when the X-plane motor 114 rotates, its rotational force is transmitted to the shaft 1c by way of the worm gear 115 and the worm wheel 1C, thereby rotating the optical base member 1 about the shafts 1b and 1c. Thus, an angle of the optical base member 1 with respect to the object 4 on the X-plane can be changed while holding the housing 2 fixed position relative to the object 4.

The motors 113 and 114 of the third colorimeter are driven as follows. The X-plane motor 114 is driven in the forward direction if the posture is inclined in the plus direction on the X-plane, while being driven in the reverse direction if it is inclined in the minus direction on the X-plane. The Y-plane motor 113 is driven in the forward direction if the posture is inclined in the plus direction on the Y-plane, while being driven in the reverse direction if it is inclined in the minus direction on the Y-plane.

An electrical construction of the third colorimeter is identical to that of the first colorimeter shown in FIG. 5 except for the fact that the motors 94 and 94' in FIG. 5 are replaced with the motors 113 and 114. As for the color measurement of the third colorimeter, it is similar to the first colorimeter. Only differences are: the X-plane motor 114 is driven in the forward direction (Step #86), the X-plane motor 114 is driven in the reverse direction (Step #88) and the driving of the X-plane motor 114 is stopped (Step #92); and the Y-plane motor 113 is driven in the forward direction (Step #100), the Y-plane motor 113 is driven in the reverse direction (Step #102) and the driving of the Y-plane motor 113 is stopped (Step #106).

As for the judgments made in Steps #90 and #104, an inclining range of the optical base member 1 may be defined by specified angles with respect to the object 4 and a judgment may be made as to whether the optical base member 1 has been inclined beyond this range. No further description is given on the third colorimeter as the circuit construction and operation sequence of the third colorimeter are easily understandable from the first colorimeter.

Figure 22A:
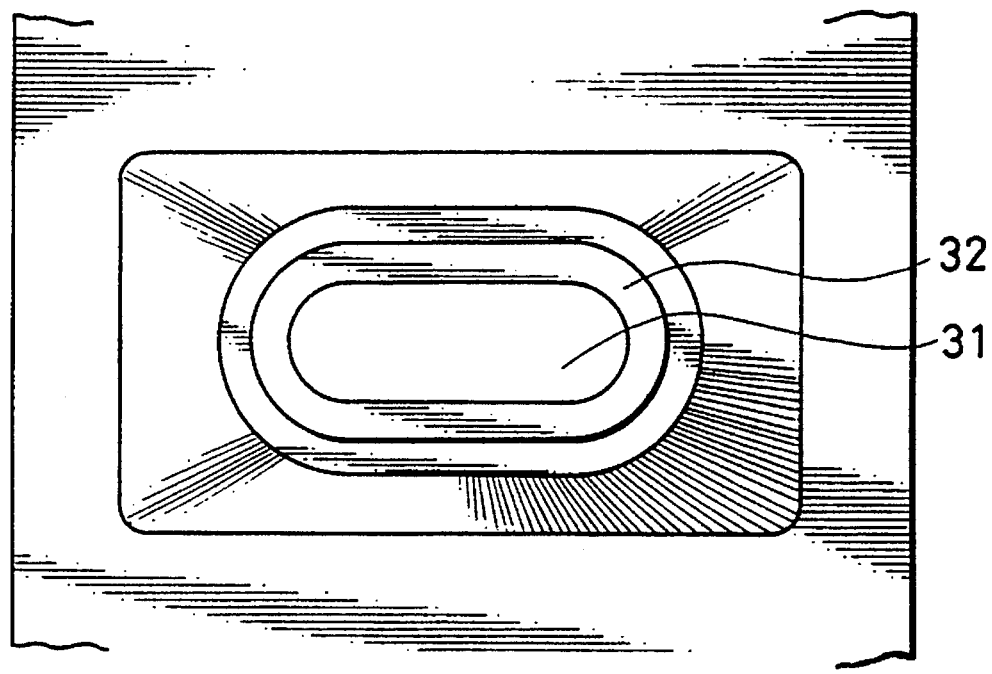
FIG. 22A is a bottom view showing a foot member of the first colorimeter.
Figure 22B:
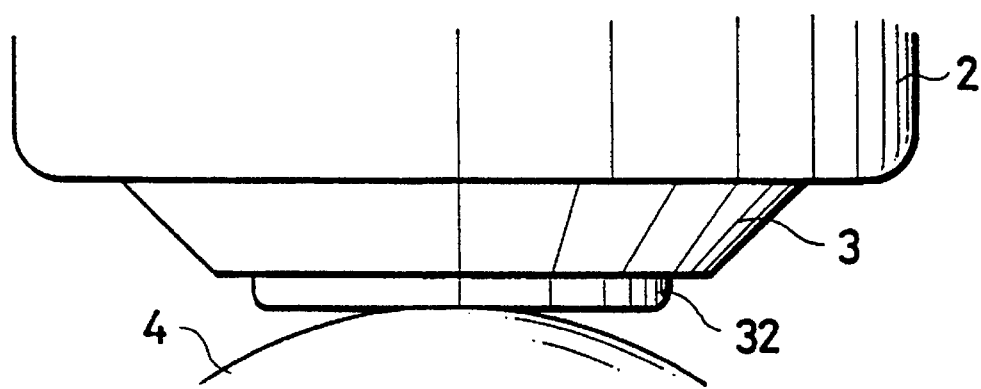
FIG. 22B is a front view showing the foot member of the first colorimeter.
Figure 23A:
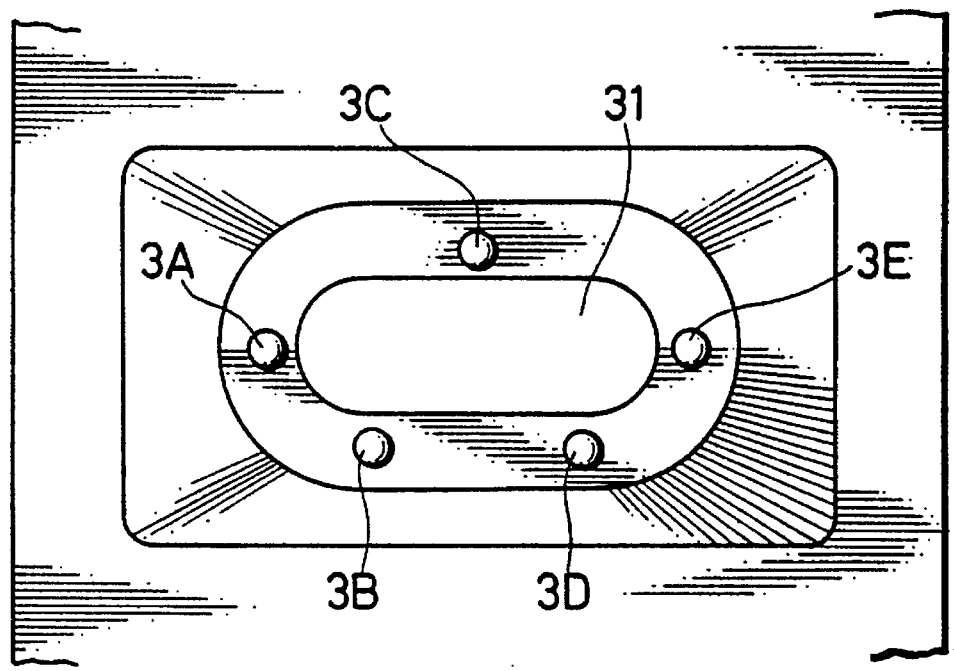
FIG. 23A is a bottom view showing foot members of the third colorimeter.
Figure 23B:
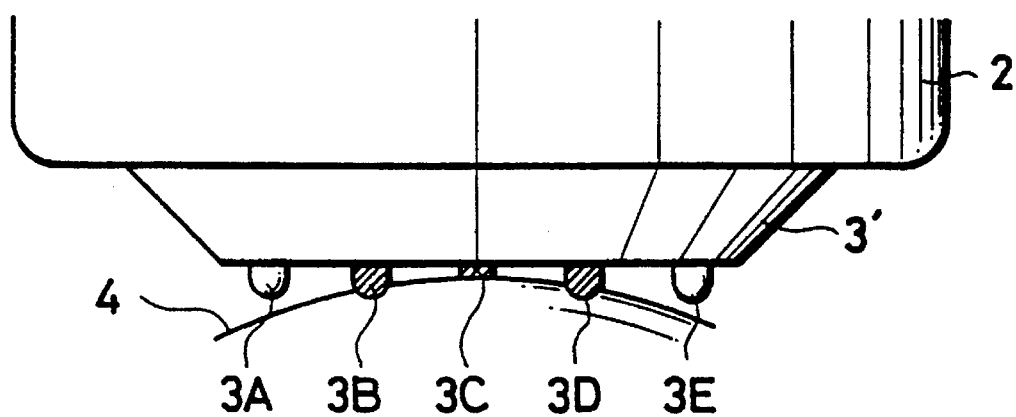
FIG. 23B is a front view showing the foot members of the third colorimeter.

Next, description of a measurement foot member of the present invention is made. FIGS. 22A and 22b shows a measurement foot member of the first colorimeter while FIGS. 23A and 23B show a measurement foot member of the third colorimeter.

In the first colorimeter, the measurement foot member 3 is formed at the periphery of its opening 31 with an annular projection 32 which projects downward by a specified distance, and the projection 32 is brought into contact with the surface of the object 4. However, a contact of this measurement foot member 3 with the object 4 is planar. Accordingly, if the object 4 has a curved surface, the measurement foot member 3 cannot stably support the colorimeter.

However, in the first colorimeter, since the posture adjustment is made by integrally driving the optical base member 1 and the housing 2, i.e., by driving the entire colorimeter, the colorimeter can be held in proper posture by the posture adjusting mechanisms 9 even if the support of the measurement foot member 3 is unstable for a curved surface.

In the third colorimeter, the posture adjustment is made by driving only the optical base member 1 while fixing the housing 2. Accordingly, the colorimeter needs to stably be held relative to the object 4.

FIGS. 22C and 22D show a structure of the measurement foot member 3' capable of stably supporting the colorimeter even when the object 4 has a spherical or curved surface.

In place of the projection 32 of the first colorimeter, there are five downward projecting five projections 3A, 3B, 3C, 3D and 3E of the same size which are arranged on the periphery of an opening 31' of the measurement foot member 3', e.g., at specified intervals when viewed from front.

With this measurement foot member 3', all five projections 3A to 3E are brought into contact with the object 4 when the object 4 has a flat surface, thereby stably supporting the colorimeter at five contact points. On the other hand, when the object 4 has a spherical or curved surface, three out of the five projections, namely 3B, 3C and 3D, are brought into contact with the object 4, thereby supporting the colorimeter at three contact points. By forming the projections 3A to 3E on the periphery of the opening 31' of the measurement foot member 3', the measurement foot member 3' is enabled to stably support the colorimeter when the object 4 has a spherical surface as well as when it has a flat surface.

The foregoing embodiments connection with a colorimeter in which light projected from one light projector is received by photosensors disposed at different angle positions. However, the present invention is not limited to such constructions. For example, it may be appreciated to provide a plurality of light projectors at different angle positions and one photosensor.

In the foregoing embodiments, also, the present invention is described with reference to a colorimeter for determining the color of an object. However, the present invention may be applied to any measuring apparatus such as a glossimeter for measuring the gloss, and a densitometers for measuring the concentration, which needs to be adjusted to have a specified posture with respect to an object.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. An apparatus for measuring color of an object, the apparatus comprising:

a primary light projector which projects light to an object;

a primary photosensor which senses light which has been projected by the light projector and reflected from the object;

a calculator which calculates a color value of the object based on an output of the primary photosensor;

an angle detector which detects respective angles of the primary light projector and the primary photosensor with respect to the object;

an adjustment mechanism which adjusts the respective angles of the primary light projector and the primary photosensor; and a controller which controls the adjustment mechanism based on a detection result of the angle detector so that the primary light projector and the primary photosensor come into their respective desired angles.

2. An apparatus according to claim 1, wherein the angle detector includes:

a secondary light projector which project a spotlight to the object:

secondary photosensor which senses light which has been projected by the secondary light projector and reflected from the object:

a judgment device which judges based on an output of the secondary photosensor the respective angles of the primary light projector and the primary photosensor with respect to the object.

3. An apparatus according to claim 1, further comprising a display device which displays the detected angles of the primary light projector and the photosensor.

4. An apparatus according to claim 1, further comprising a housing which accommodates the primary light projector, the primary photosensor, the calculator, the angle detector, and the adjustment mechanism, wherein the adjustment mechanism includes:

a base member which carries the primary light projector and the primary photosensor, and is movable in relative to the housing; and a driver which drives the base member to adjust the respective angles of the primary light projector and photosensor.

5. An apparatus according to claim 1, further comprising a housing which accommodates the primary light projector, the primary photosensor, the calculator, the angle detector, and the adjustment mechanism, wherein the adjustment mechanism includes:

a support member which supports a specified portion of housing, and is movable in relative to the housing; and a driver which drives the support member to adjust the respective angles of the primary light projector and photosensor.

6. An apparatus according to claim 1, wherein the primary light projector projects light to the object at a single angle with respect to the object, and the photosensor senses the reflected light from the object at a plurality of different angles with respect to the object.

7. An apparatus according to claim 1, wherein the primary light projector projects light to the object at a plurality of different angles with respect to the object, and the photosensor senses the reflected light from the object at a single angle with respect to the object.

* * * * *